United States Patent [19]

Buchmann et al.

[11] Patent Number: 6,160,012
[45] Date of Patent: Dec. 12, 2000

[54] LEUKOTRIENE $B_4$ DERIVATIVES, IN PARTICULAR OXIMO-$LTB_4$- ANTAGONISTS

[75] Inventors: Bernd Buchmann, Neuendorf; Wolfgang Frohlich, Berlin; Claudia Giesen, Berlin; Hartwig Hennekes, Berlin; Stefan Jaroch, Berlin; Werner Skuballa, Berlin, all of Germany

[73] Assignee: Schering Aktiengesellschaft, Berlin, Germany

[21] Appl. No.: 09/423,336

[22] PCT Filed: May 22, 1998

[86] PCT No.: PCT/EP98/03139

§ 371 Date: Mar. 27, 2000

§ 102(e) Date: Mar. 27, 2000

[87] PCT Pub. No.: WO98/52915

PCT Pub. Date: Nov. 26, 1998

[30] Foreign Application Priority Data

May 23, 1997 [DE] Germany ............... 197 22 848

[51] Int. Cl.$^7$ ............... C07C 405/00; A01K 31/5575
[52] U.S. Cl. ............... 514/530; 514/567; 560/35; 562/440
[58] Field of Search ............... 560/35; 562/440; 514/530, 567

[56] References Cited

FOREIGN PATENT DOCUMENTS

98/52195  5/1998  WIPO ............... 514/530

*Primary Examiner*—Robert Gerstl
*Attorney, Agent, or Firm*—Millen, White, Zelano & Branigan, P.C.

[57] ABSTRACT

Leukotriene-$B_4$ derivatives of general formula (I), in which $R_1$ represents H, $CF_3$, $CH_2OH$, and $R_2$ represents H or an organic acid radical; $R^3$ symbolizes H, $C_1$–$C_{14}$ alkyl, $C_3$–$C_{10}$ cycloalkyl, or a 5- to 6-membered aromatic heterocyclic ring with at least 1 heteroatom; $R_4$ means hydrogen, $C_1$–$C_{10}$ alkyl, $C_3$–$C_{10}$ cycloalkyl; A symbolizes a trans, trans—CH=CH—CH=CH, a —$CH_2CH_2$—CH=CH— or a tetramethylene group; B symbolizes a $C_1$–$C_{10}$— straight-chain or branched-chain alkylene group or group (a) or (b); D can mean a direct bond, oxygen, sulfur, —C≡C—, —CH=$CR_7$, or together with B can also mean a direct bond; $R_5$ and $R_6$ are the same or different and represent H or $C_1$–$C_4$ alkyl, or $R_6$ represents H and $R_5$ represents $C_1$–$C_{15}$ alkanoyl or $R_8$ represents $SO_2$; $R_7$ means H, $C_1$–$C_5$ alkyl, chlorine, bromine; $R_8$ has the same meaning as $R_3$, m means 1–3, o means 0–5, p means 0–5, X is a direct bond, oxygen, sulfur, an aromatic compound or heteroaromatic compound, Y is a $C_1$–$C_8$ alkyl, $C_3$–$C_{10}$ cycloalkyl, n is 2–5, and, if $R_4$ means hydrogen, their salts with physiologically compatible bases and their cyclodextrin clathrates. The leukotriene derivatives are used as dermatological products.

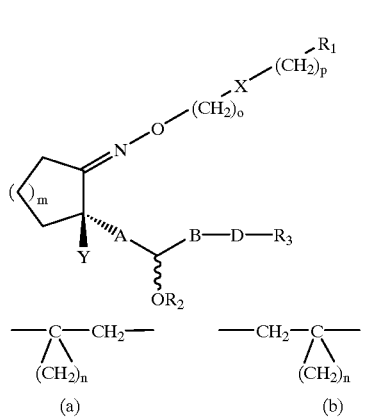

3 Claims, No Drawings

LEUKOTRIENE B₄ DERIVATIVES, IN PARTICULAR OXIMO-LTB₄- ANTAGONISTS

The invention relates to new leukotriene-$B_4$ derivatives, process for their production and their use as pharmaceutical agents. The new compounds are optically active structural analogues of previously known leukotriene-$B_4$ antagonists, which contain a six-membered ring as a basic structural element (DE-A 39 17 597, DE-A 42 27 790.6, DE 42 42 390).

The physiological and especially the pathophysiological importance of leukotriene $B_4$ is summarized in several more recent works: a) The Leukotrienes, Chemistry and Biology eds. L. W. Chakrin, D. M. Bailey, Academic Press 1984. b) J. W. Gillard et al., Drugs of the Future 12, 453 (1987). c) B. Samuelsson, Sciences 237, 1171 (1987). d) C. W. Parker, Drug Development Research 10, 277 (1987). e) W. R. Henderson, Annals of Internal Medicine 121, 684 (1994). It follows from the above that $LTB_4$ is an important inflammation mediator for inflammatory diseases, in which leukocytes invade the affected tissue.

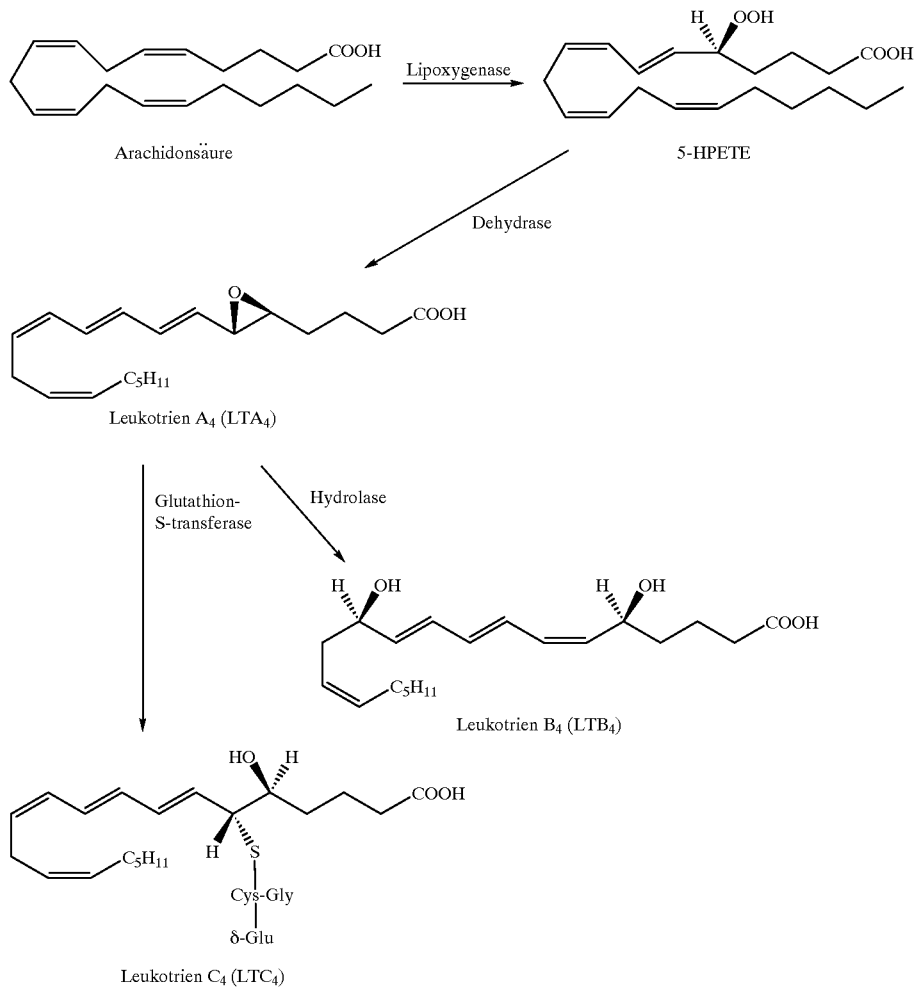

KEY:
Arachidonsäure=arachidonic acid
Leukotrien $A_4$ ($LTA_4$)=leukotriene $A_4$ ($LTA_4$)
Glutathion–S-transferase=glutathione–S-transferase
Leukotrien $B_4$ ($LTB_4$)=leukotriene $B_4$ ($LTB_4$)
Leukotrien $C_4$ ($LTC_4$)=leukotriene $C_4$ ($LTC_4$)

Leukotriene $B_4$ ($LTB_4$) was discovered by B. Samuelsson et al. as a metabolite of the arachidonic acid. In the biosynthesis, leukotriene $A_4$ is formed by the enzyme 5-lipoxygenase first as a central intermediate product, which then is converted by a specific hydrolase into the $LTB_4$.

The nomenclature of the leukotrienes can be deduced from the following works:

a) B. Samuelsson et al., Prostaglandins 19, 654 (1980); 17, 785 (1979).

b) C. N. Serhan et al., Prostaglandins 34, 201 (1987).

The effects of $LTB_4$ are triggered on the cellular plane by the binding of $LTB_4$ to a specific receptor.

It is known concerning $LTB_4$ that it causes the adhesion of leukocytes to the blood vessel wall. $LTB_4$ is chemotactically active, i.e., it triggers a directed migration of leukocytes in the direction of a gradient of increasing concentration. Furthermore, it indirectly changes the vascular permeability based on its chemotactic activity, whereby a synergism with prostaglandin $E_2$ is observed. $LTB_4$ obviously plays a decisive role in inflammatory, allergic and immunological processes.

Leukotrienes and especially $LTB_4$ are involved in skin diseases, which are accompanied by inflammatory processes (increased vascular permeability and formation of edemas, cell infiltration), increased proliferation of skin cells and itching, such as, for example, in eczemas, erythemas, psoriasis, pruritus and acne. Pathologically increased leukotriene concentrations are involved either causally in the development of many dermatitides or there is a connection between the persistence of the dermatitides and the leukotrienes. Clearly increased leukotriene concentrations were measured, for example, in the skin of patients with psoriasis, atopic dermatitis, allergic contact dermatitis, bullous pemiphigoids, delayed duchurticaria and allergic vasculitis.

Leukotrienes and especially $LTB_4$ are also involved in the diseases of internal organs, for which an acute or chronic inflammatory component was described, e.g.: joint diseases (rheumatic arthritis); diseases of the respiratory tract (asthma and chronically obstructive lung diseases (OPD)); inflammatory intestinal diseases (ulcerous colitis and Crohn's disease); as well as reperfusion damages (to the heart, intestinal or renal tissues), which result by the temporary pathological obstruction of blood vessels, such as glomerulonephritis, NSAID gastropathies, multiple sclerosis, rhinitis and inflammatory eye diseases.

Further, leukotrienes and especially $LTB_4$ are involved in the disease of multiple sclerosis and in the clinical appearance of shock (triggered by infections, burns or in complications in kidney dialysis or other separately discussed perfusion techniques).

In addition, leukotrienes and especially $LTB_4$ have an effect on the formation of white blood cells in the bone marrow, on the growth of unstriped muscle cells, of keratinocytes and of B-lymphocytes. $LTB_4$ is therefore involved in diseases with inflammatory processes and in diseases with pathologically increased formation and growth of cells.

For example, leukemia or arteriosclerosis represent diseases with this clinical appearance.

Leukotrienes and especially $LTB_4$ and its derivatives are suitable for reducing elevated triglyceride levels and thus act in an anti-arteriosclerotic manner and against obesity.

By the antagonizing of the effects, especially by $LTB_4$, the active ingredients and their forms for dispensing of this invention are specific medicines for diseases of humans and animals, in which especially leukotrienes play a pathological role.

Besides the therapeutic possibilities, which can be derived from an antagonizing of $LTB_4$ action with $LTB_4$ analogs, the usefulness and potential use of leukotriene-$B_4$ agonists for the treatment of fungus diseases of the skin were also able to be shown (H. Katayama, Prostaglandins 34, 797 (1988)).

The invention relates to leukotriene-$B_4$ derivatives of general formula I

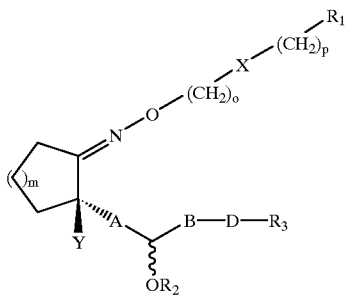

in which
$R_1$ represents H, $CF_3$, $CH_2OH$, $COOR_4$, $CONR_5R_6$, and
$R_2$ represents H or an organic acid radical with 1–15 C atoms,
$R_3$ symbolizes H; $C_1$–$C_{14}$ alkyl, $C_3$–$C_{10}$ cycloalkyl optionally substituted in one or more places; $C_6$–$C_{10}$ aryl radicals, independently of one another, optionally substituted in one or more places by halogen, phenyl, $C_1$–$C_4$ alkyl, $C_1$–$C_4$ alkoxy, fluoromethyl, chloromethyl, trifluoromethyl, carbonyl, carboxyl or hydroxyl; or a 5- to 6-membered aromatic heterocyclic ring with at least 1 heteroatom,
$R_4$ means hydrogen, $C_1$–$C_{10}$ alkyl, $C_3$–$C_{10}$ cycloalkyl; $C_6$–$C_{10}$ aryl radicals optionally substituted by 1–3 halogen, phenyl, $C_1$–$C_4$ alkyl, $C_1$–$C_4$ alkoxy, fluoromethyl, chloromethyl, trifluoromethyl, carboxyl or hydroxyl; $CH_2$—CO—($C_6$–$C_{10}$) aryl or a 5- to 6-membered ring with at least 1 heteroatom,
A symbolizes a trans, trans-CH=CH—CH=CH, a —$CH_2CH_2$—CH=CH— or a tetramethylene group,
B symbolizes a $C_1$–$C_{10}$ straight-chain or branched-chain alkylene group, which optionally can be substituted by fluorine or the group

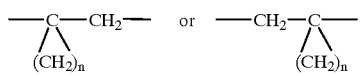

D means a direct bond, oxygen, sulfur, —C≡C—, —CH=CR$_7$, or together with B can also mean a direct bond,
$R_5$ and $R_6$ are the same or different, and represent H or $C_1$–$C_4$ alkyl optionally substituted by hydroxy groups, or $R_6$ represents H and $R_5$ represents $C_1$–$C_{15}$ alkanoyl or $R_8SO_2$,
$R_7$ means H, $C_1$–$C_5$ alkyl, chlorine, bromine,
$R_8$ has the same meaning as $R_3$,
m means 1–3,
o means 0–5,
p means 0–4,
X is a direct bond, oxygen, sulfur, an aromatic compound or heteroaromatic compound,
Y is a $C_1$–$C_8$ alkyl optionally substituted in one or more places, $C_3$–$C_{10}$ cycloalky, optionally substituted by aryl,
n is 2–5,
and, if $R_4$ means hydrogen, their salts with physiologically compatible bases and their cyclodextrin clathrates.

The group $OR_2$ can be in α- or β-position. Formula I comprises both racemates and the possible pure diastereomers and enantiomers. The stereochemistry of the oxime double bond can be E- or Z-configured; preferably E-configured oximes are obtained.

As alkyl groups $R_4$, straight-chain or branched-chain alkyl groups with 1–10 C atoms are considered, such as, for example, methyl, ethyl, propyl, butyl, isobutyl, tert-butyl, pentyl, neopentyl, hexyl, heptyl, decyl.

Alkyl groups $R_4$ can optionally be substituted in one or more places by halogen atoms, alkoxy groups, optionally substituted aryl or aroyl groups with 6–10 C atoms (relative to possible substituents, see under aryl $R_4$), dialkylamino and trialkylammonium with 1–4 C atoms in the alkyl portion, whereby single substitution is to be preferred. As substituents, for example, fluorine, chlorine or bromine, phenyl, dimethylamino, diethylamino, methoxy, ethoxy can be mentioned. As preferred alkyl groups $R_4$, those with 1–4 C atoms can be mentioned.

Cycloalkyl group $R_4$ can contain 3–10, preferably 5 and 6 carbon atoms in the ring. The rings can be substituted by alkyl groups with 1–4 carbon atoms. For example, cyclopentyl, cyclohexyl, methylcyclohexyl can be mentioned.

As aryl groups $R_4$, both substituted and unsubstituted aryl groups with 6–10 C atoms are considered, such as, for example, phenyl, 1-naphthyl and 2-naphthyl, which can be substituted in each case by 1–3 halogen atoms (F, Cl, Br), a phenyl group, 1–3 alkyl groups with, in each case, 1–4 C atoms, a chloromethyl, a fluoromethyl, trifluoromethyl, carboxyl, hydroxyl or alkoxy group with 1–4 C atoms. Preferred substituents in 3- and 4-position on the phenyl ring are, for example, fluorine, chlorine, alkoxy or trifluoromethyl, in 4-position, however, hydroxyl.

As heterocyclic groups $R_4$, 5- and 6-membered aromatic heterocycles that contain at least 1 heteroatom, preferably nitrogen, oxygen or sulfur, are suitable. For example, 2-furyl, 2-thienyl, 2-pyridyl, 3-pyridyl, 4-pyridyl, oxazolyl, thiazolyl, pyrimidinyl, pyridazinyl, 3-furyl, 3-thienyl, 2-tetrazolyl, i.a., can be mentioned.

As acid radical $R_5$, such physiologically compatible acids are suitable. Preferred acids are organic carboxylic acids and sulfonic acids with 1–15 carbon atoms, which belong to the aliphatic, cycloaliphatic, aromatic, aromatic-aliphatic and heterocyclic series. These acids can be saturated, unsaturated and/or polybasic and/or substituted in the usual way. As examples of the substituents, $C_{1-4}$ alkyl, hydroxyl, $C_{1-4}$ alkoxy, oxo or amino groups or halogen atoms (F, Cl, Br) can be mentioned. For example, the following carboxylic acids can be mentioned: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid; benzoic acids substituted with halogen (F, Cl, Br) or trifluoromethyl, hydroxy, $C_{1-4}$ alkoxy or carboxy groups; nicotinic acid, isonicotinic acid, furan-2-carboxylic acid, cyclopentylpropionic acid. As preferred arylsulfonyl radicals and alkanesulfonyl radicals $R_8SO_2$, those are to be considered that are derived from a sulfonic acid with up to 10 carbon atoms. As sulfonic acids, for example, methanesulfonic acid, ethanesulfonic acid, isopropanesulfonic acid, cyclohexanesulfonic acid, benzenesulfonic acid, p-toluenesulfonic acid, p-chlorobenzenesulfonic acid, N,N-dimethylaminosulfonic acid, N,N-diisobutylaminosulfonic acid, N,N-dibutylaminosulfonic acid, pyrrolidino, piperidino, piperazino, M-methylpiperazino and morpholinosulfonic acid are suitable.

As alkyl groups $R_3$, straight-chain and branched-chain, saturated and unsaturated alkyl radicals, preferably saturated, with 1–14, especially 1–10 C atoms, are suitable, which optionally can be substituted by optionally substituted phenyl (for substitution, see under aryl $R_5$). For example, methyl, ethyl, propyl, butyl, isobutyl, tert-butyl, pentyl, hexyl, heptyl, octyl, butenyl, isobutenyl, propenyl, pentenyl, benzyl, m- and p-chlorobenzyl groups can be mentioned. If alkyl groups $R_3$ are halogen-substituted, fluorine, chlorine and bromine are suitable as halogens.

As examples of halogen-substituted alkyl groups $R_3$, alkyls with terminal trifluoromethyl groups are considered.

Cycloalkyl group $R_3$ can contain 3–10, preferably 3–6 carbon atoms in the ring. The rings can be substituted by alkyl groups with 1–4 carbon atoms optionally by halogens. For example, cyclopropyl, cyclobutyl, cyclopentyl, cyclohexyl, methyl-cyclohexyl, fluorocyclohexyl can be mentioned.

As substituted or unsubstituted aryl groups $R_3$, for example, phenyl, 1-naphthyl and 2-naphthyl, which can be substituted in each case by 1–3 halogen atoms (F, Cl, Br), a phenyl group, 1–3 alkyl groups with 1–4 C atoms in each case, a chloromethyl, fluoromethyl, trifluoromethyl, carboxyl, $C_1$–$C_4$ alkoxy or hydroxyl group, are considered. Preferred is the substitution in 3- and 4-position on the phenyl ring by, for example, fluorine, chlorine, alkoxy or trifluoromethyl or in 4-position by hydroxyl.

As heterocyclic aromatic groups $R_3$, 5- and 6-membered heterocycles that contain at least 1 heteroatom, preferably nitrogen, oxygen or sulfur, are suitable. For example, 2-furyl, 1-thienyl, 2-pyridyl, 3-pyridyl, 4-pyridyl, oxazolyl, thiazolyl, pyrimidinyl, pyridazinyl, pyrazinyl, 3-furyl, 3-thienyl, i.a., can be mentioned.

As alkylene group B, straight-chain or branched, saturated or unsaturated alkylene radicals, preferably saturated with 1–10, especially with 1–5 C atoms, are suitable, which optionally can be substituted by fluorine atoms. For example, methylene, fluoromethylene, difluoromethylene, ethylene, 1,2-propylene, ethylethylene, trimethylene, tetramethylene, pentamethylene, 1,2-difluoroethylene, 1-fluoroethylene, 1-methyltetramethylene, 1-methyltrimethylene, 1-methylene-ethylene, 1-methylene-tetramethylene can be mentioned.

In addition, alkylene group B can represent the group

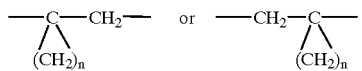

whereby n=2–5, preferably 3–5.

As acid radicals $R_2$, those of physiologically compatible acid radicals are suitable. Preferred acids are organic carboxylic acids and sulfonic acids with 1–15 carbon atoms, which belong to the aliphatic, cycloaliphatic, aromatic, aromatic-aliphatic or heterocyclic series. These acids can be substituted saturated, unsaturated and/or polybasic and/or in the usual way. As examples of the substituents, $C_{1-4}$ alkyl, hydroxyl, $C_{1-4}$ alkoxy, oxo or amino groups or halogen atoms (F, Cl, Br) can be mentioned. For example, the following carboxylic acids can be mentioned: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopentylacetic acid, cyclohexylacetic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid; benzoic acids substituted with halogen (F, Cl, Br) or trifluoromethyl, hydroxyl, $C_{1-4}$ alkoxy or carboxy groups; nicotinic acid, isonicotinic acid, furan-2-carboxylic acid, cyclopentylpropionic acid. As preferred acid radicals $R_2$ and $R_3$, those acyl radicals with up to 10 carbon atoms are considered.

Alkyl radicals $R_5$ and $R_6$, which optionally contain hydroxy groups, are straight-chain or branched alkyl radicals, especially straight-chain, such as, for example, methyl, ethyl, propyl, butyl, pentyl, hexyl, especially preferably methyl.

$R_7$ as $C_{1-5}$ alkyl means straight-chain or branched-chain alkyl radicals as were already mentioned for $R_3$ or $R_4$. Preferred alkyl radicals $R_7$ are methyl, ethyl, propyl and isopropyl.

Inorganic and organic bases are suitable for salt formation, as they are known to one skilled in the art for forming physiologically compatible salts. For example, alkali hydroxides, such as sodium hydroxide and potassium hydroxide, alkaline-earth hydroxides, such as calcium hydroxide, ammonia, amines, such as ethanolamine, diethanolamine, triethanolamine, N-methylglucamine, morpholine, tris(hydroxymethyl)-methylamine, etc., can be mentioned.

To attain the cyclodextrin clathrates, the compounds of formula I are reacted with α-, β- or γ-cyclodextrin. Preferred are β-cyclodextrin derivatives.

Preferred compounds of this invention are compounds of general formula I, whereby the radicals have the following meaning:

$R_1$ is $CF_3$, $CH_2OH$, $CONR_5R_6$, $COOR_4$ with $R_4$ in the meaning of a hydrogen atom, an alkyl radical with 1–10 C atoms, a cycloalkyl radical with 5–6 C atoms, a phenyl radical optionally substituted by 1–2 chlorine, bromine, phenyl, $C_{1-4}$ alkyl, $C_{1-4}$ alkoxy, chloromethyl, fluoromethyl, trifluoromethyl, carboxy or hydroxy, X is an aromatic compound or a direct bond, Y is a methyl group, m is 1–3, o is 1–5, p is 0,1, A is a trans-CH=CH—CH=CH or tetramethylene group;

B is a straight-chain or branched-chain, saturated or unsaturated alkylene group with up to 10 C atoms, which optionally can be substituted by fluorine, or the group

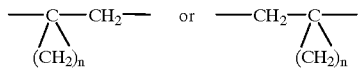

with n=2–5;

D is a direct bond, oxygen, sulfur, a —C≡C group or a —CH=$CR_7$ group with $R_7$ as hydrogen, $C_{1-5}$ alkyl, chlorine or bromine;

B and D are together a direct bond;

$R_2$ means hydrogen or an organic acid radical with 1–15 C atoms;

$R_5$ and $R_6$ have the above-indicated meanings;

$R_3$ is a hydrogen atom, $C_{1-10}$ alkyl, cycloalkyl with 5–6 C atoms, a phenyl radical optionally substituted by 1–2 chlorine, bromine, phenyl, $C_{1-4}$ alkyl, $C_{1-4}$ alkoxy, chloromethyl, fluoromethyl, trifluoromethyl, carboxyl or hydroxyl, and if $R_4$ means a hydrogen, their salts with physiologically compatible bases and cyclodextrin clathrates.

Especially preferred compounds of this invention are compounds of general formula I, whereby the radicals have the following meaning:

$R_1$ is $CF_3$, $CH_2OH$, $CONR_5R_6$, $COOR_4$ with $R_4$ in the meaning of a hydrogen atom, an alkyl radical with 1–4 C atoms, $R_2$ means hydrogen or an organic acid radical with 1–6 C atoms, $R_3$ is a hydrogen atom or $C_{1-10}$ alkyl;

$R_5$ and $R_6$ have the above-indicated meanings;

A is a trans, trans-CH=CH—CH=CH or tetramethylene group;

B is a straight-chain or branched-chain alkylene group with up to 5 C atoms, or the group

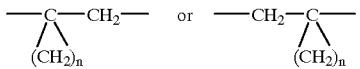

with n=3,4;

D is a direct bond or a —C≡C group or a —CH=$CR_7$ group with $R_7$ as hydrogen or $C_{1-5}$ alkyl;

X is a direct bond or an aromatic compound,

Y is a methyl group, m is 2, o is 1–5, p is 0, 1,

B and D are together a direct bond;

and if $R_4$ means a hydrogen atom, their salts with physiologically compatible bases and their cyclodextrin clathrates.

In addition, the invention relates to a process for the production of the compounds of general formula I according to the invention, which is characterized in that a ketone of formula II,

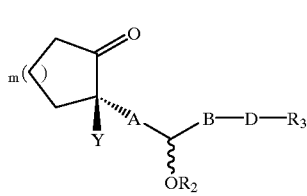

in which A, B, D, m, $R_2$, $R_3$ and Y have the above-indicated meaning, optionally under protection of free hydroxy groups in $R_2$, is reacted with a hydroxylamine or a hydroxylammonium salt and then with an alkylating reagent of general formula III, $$E—(CH_2)_o—X—(CH_2)_p—R_1 \quad (III)$$

whereby E represents a halide or sulfonate, and o, X, p, and $R_1$ have the above-indicated meanings, is reacted in the presence of a base and optionally then separated in any sequence of isomers, protected hydroxy groups are released and/or a free hydroxy group is etherified and/or a carboxyl group is reduced and/or a carboxyl group is esterified and/or a carboxyl group is converted into an amide or a carboxyl group is converted into a salt with a physiologically compatible base. As halides according to general formula III, chlorine, bromine, iodine are suitable, and as sulfonates, mesylate, tosylate and triflate are suitable.

The reaction of the compound of general formula II with a hydroxylammonium salt is performed at temperatures of 0° C. to 100° C., preferably at 25° C., in a solvent mixture that consists of an aprotic solvent, such as, e.g., tetrahydrofuran or pyridine, and a protic solvent or solvent mixture, such as water and/or alcohols.

The etherification of the oximes with alkylating agents of general formula III is carried out in a known way in an aprotic solvent or solvent mixture, for example dimethylformamide or tetrahydrofuran or dimethoxyethane, under the action of a base at 0–30° C. As a base, for example, sodium hydride is suitable.

The esterification of the alcohols of formula I ($R_2$=H) is carried out in a way that is known in the art. For example, the esterification is carried out in that an acid derivative, preferably an acid halide or acid anhydride, is reacted with an alcohol of formula I in the presence of a base such as, for example, sodium hydride, pyridine, triethylamine, tributylamine or 4-dimethylaminopyridine. The reaction can be performed without a solvent or in an inert solvent, preferably acetone, acetonitrile, dimethylacetamide, dimethyl sulfoxide at temperatures above or below room temperature, for example, between −80° C. to 100° C., preferably at room temperature.

The reduction to the compounds of formula I with $R_1=CH_2OH$ is performed with a reducing agent that is suitable for the reduction of esters or carboxylic acids, such as, for example, lithium aluminum hydride, diisobutyl aluminum hydride, etc. As a solvent, diethyl ether, tetrahydrofuran, dimethoxyethane, toluene, etc., are suitable. The reduction is performed at temperatures of −30° C. up to boiling temperature of the solvent, preferably 0° C. to 30° C.

The etherification of the alcohols of formula I (with $R_1=CH_2OH$ and p=0 and X=a direct bond) to compounds of general formula I (with X=0 and p=1–4) is carried out in a way that is known in the art. For example, the etherification is carried out in that the alcohol of general formula I ($R_1=CH_2OH$), optionally after protection of present free hydroxy groups with a halocarboxylic acid derivative or haloalkyl derivative of general formula IV,

$$\text{Hal-}(CH_2)_p\text{—}R_1 \qquad (IV)$$

whereby Hal is a chlorine, bromine or iodine atom and $R_1$ has the above-indicated meaning, is reacted in the presence of a base, and then optionally $R_1$, as described above, is further functionalized. The reaction of the compound of general formula I with a halogen compound of general formula IV is performed at temperatures of 0° C. to 100° C., preferably 10° C. to 80° C., in an aprotic solvent or solvent mixture, for example dimethyl sulfoxide, dimethylformamide, tetrahydrofuran, toluene, etc. As bases, the bases that are known to one skilled in the art for etherification are suitable, for example sodium hydride, potassium-tert-butylate, butyllithium. The above-mentioned etherification can also be performed preferably under phase-transfer conditions with 20–50% aqueous sodium hydroxide or potassium hydroxide solution without an additional solvent or in an aprotic solvent, such as, for example, toluene in the presence of a phase-transfer catalyst such as tetrabutylammonium hydrogen sulfate at temperatures of between 0° C. and 90° C., preferably between 20° C. and 60° C.

The saponification of the esters of formula I is performed according to the methods that are known to one skilled in the art, such as, for example, with basic catalysts. The compounds of formula I can be separated by the conventional separating methods into optical isomers (Asymmetric Synthesis, Vol. 1–5, Ed. J. D. Morrison, Academic Press, Inc., Orlando etc., 1985; Chiral Separations by HPLC, Ed. A. M. Krstulovic; John Wiley & Sons; New York etc. 1989).

The release of the protected hydroxyl groups is carried out according to known methods. For example, the cleavage of hydroxyl protective groups, such as, for example, the tetrahydropyranyl radical, is performed in an aqueous solution of an organic acid, such as, e.g., oxalic acid, acetic acid, propionic acid, i.a., or in an aqueous solution of a mineral acid, such as, e.g., hydrochloric acid. To improve the solubility, a water-miscible inert organic solvent is suitably added. Suitable organic solvents are, e.g., alcohols, such as methanol and ethanol, and ethers, such as dimethoxyethane, dioxane and tetrahydrofuran. Tetrahydrofuran is preferably used. The cleavage is performed preferably at temperatures of between 20° C. and 80° C. The cleavage of the silyl ether protective groups is carried out, for example, with tetrabutylammonium fluoride or with potassium fluoride in the presence of a crown ether (such as, for example, dibenzo [18]-crown-6). As a solvent, for example, tetrahydrofuran, diethyl ether, dioxane, dichloromethane, etc., are suitable. The cleavage is performed preferably at temperatures of between 0° C. and 80° C.

The saponification of the acyl groups is carried out, for example, with alkali or alkaline-earth carbonates or -hydroxides in an alcohol or in the aqueous solution of an alcohol. As an alcohol, lower aliphatic alcohols, such as, e.g., methanol, ethanol, butanol, etc., preferably methanol, are considered. As alkali carbonates and -hydroxides, potassium, sodium and cesium salts can be mentioned. Preferred are potassium salts.

As alkaline-earth carbonates and -hydroxides, for example, calcium carbonate, calcium hydroxide and barium carbonate are suitable. The reaction is carried out at −10° C. to +70° C., preferably at +25° C.

The introduction of ester group —$COOR_4$ for $R_1$, in which $R_4$ represents an alkyl group with 1–10 C atoms, is carried out according to the methods that are known to one skilled in the art. The 1-carboxy compounds are reacted, for example, with diazohydrocarbons in a way that is known in the art. The esterification with diazohydrocarbons is carried out, e.g., in that a solution of the diazohydrocarbon in an inert solvent, preferably in diethyl ether, is mixed with the 1-carboxy compound in the same solvent or in another inert solvent, such as, e.g., methylene chloride. After the reaction is completed in 1 to 30 minutes, the solvent is removed, and the ester is purified in the usual way. Diazoalkanes are either known or can be produced according to known methods [Org. Reactions Vol. 8, pages 389–394 (1954)].

The introduction of ester group —$COOR_4$ for $R_1$, in which $R_4$ represents a substituted or unsubstituted aryl group, is carried out according to the methods that are known to one skilled in the art. For example, the 1-carboxy compounds are reacted in an inert solvent with the corresponding arylhydroxy compounds with dicyclohexylcarbodiimide in the presence of a suitable base, for example, pyridine, dimethylaminopyridine, triethylamine. As a solvent, methylene chloride, ethylene chloride, chloroform, ethyl acetate, tetrahydrofuran, preferably chloroform, are suitable. The reaction is performed at temperatures of between −30° C. and +50° C., preferably at 10° C.

The leukotriene-$B_4$ derivatives of formula I with $R_4$ meaning a hydrogen can be converted into a salt with suitable amounts of the corresponding inorganic bases with neutralization. For example, in dissolving the corresponding acids in water, which contains the stoichiometric amount of the base, the (solid inorganic) salt is obtained after water is evaporated or after a water-miscible solvent, e.g., alcohol or acetone, is added.

For the production of an ammonium salt, the free acid is dissolved in, e.g., a suitable solvent, for example, ethanol, acetone, diethyl ether, acetonitrile or benzene, and at least the stoichiometric amount of the amine is added to the solution. In this way, the salt usually accumulates in solid form or is isolated after the solvent is evaporated in the usual way.

The introduction of amide group —$CONHR_5$ with $R_5$ in the meaning of alkanoyl is carried out according to the methods that are known to one skilled in the art. The carboxylic acids of formula I ($R_4=H$) are first converted into the mixed anhydride in the presence of a tertiary amine, such as, for example, triethylamine, with isobutyl chloroformate. The reaction of the mixed anhydride with the alkali salt of the corresponding amide or with ammonia ($R_5$=H) is carried out in an inert solvent or solvent mixture, such as, for example, tetrahydrofuran, dimethoxyethane, dimethylformamide, hexamethylphosphoric acid triamide, at temperatures of between −30° C. and +60° C., preferably at 0° C. to 30° C. Another type of production of the amides involves the amidolysis of 1-ester ($R_1$=$COOR_4$) with the corresponding amine.

Another possibility for the introduction of amide group —$CONHR_5$ consists in the reaction of a 1-carboxylic acid of formula I ($R_4$=H), in which free hydroxy groups are optionally intermediately protected, with compounds of formula IV, $$O=C=N-R_5 \qquad (IV)$$

in which $R_5$ has the above-indicated meaning.

The reaction of the compound of formula I ($R_4$=H) with an isocyanate of formula IV is carried out optionally with the addition of a tertiary amine, such as, e.g., triethylamine or pyridine. The reaction can be performed without a solvent or in an inert solvent, preferably acetonitrile, tetrahydrofuran, acetone, dimethylacetamide, methylene chloride, diethyl ether, toluene, at temperatures of between −80° C. to 100° C., preferably at 0° C. to 30° C.

For the production of the other amides, for example, the desired acid anhydride can be reacted with ammonia or the corresponding amines.

If the starting product contains OH groups, these OH groups are also brought to reaction. If end products that contain free hydroxyl groups are ultimately desired, a start is suitably made from starting products in which the latter are intermediately protected by preferably readily cleavable ether or acyl radicals.

The separation of the diastereomers is carried out according to the methods that are known to one skilled in the art, for example by column chromatography.

The compounds of general formula II that are used as starting material can be produced, for example, by an ester of general formula V ((a) K. Sakai et al., Tetrahedron 50, 3315 (1995); b) K. Koga et al., Tetrahedron 49, 1579 (1993)),

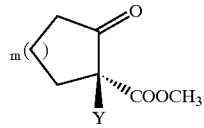
(V)

in which m and Y have the above-indicated meanings, being ketalized with ethylene glycol, reduced with diisobutylaluminum hydride and then oxidized to the aldehyde of general formula VI with the Collins reagent or by the Swern process (Tetrahedron Letters 34, 1651 (1978)) in a way that is known in the art.

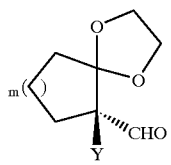
(VI)

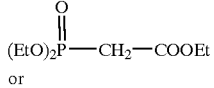
(VII)

or

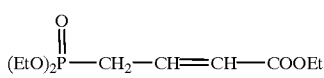
(VIII)

The Wittig-Horner olefination of aldehyde VI with the phosphonate of formula VII and a base and optionally subsequent hydrogenation as well as subsequent reduction of the ester group, oxidation of the primary alcohol, repeated Wittig-Horner olefination with the phosphonate of formula VII and optionally subsequent hydrogenation or a Wittig-Horner reaction of aldehyde VI with a phosphonate of formula VIII provides the esters of general formula IX, whereby

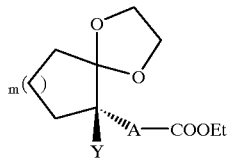
(IX)

m, y and A have the above-indicated meanings. As bases, for example, potassium-tert-butylate, diazabicyclononane, diazabicycloundecane or sodium hydride are suitable. Reduction of the ester group, for example with diisobutyl aluminum hydride, and subsequent oxidation of the primary alcohol that is obtained, e.g., with manganese dioxide or Collins reagent, results in an aldehyde of formula X.

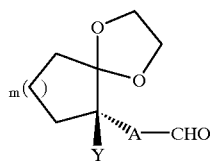
(X)

The organometallic reaction of the aldehyde of formula X with a Grignard reagent of formula XI, in which B, D

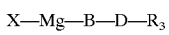
(XI)

and $R_3$ have the above-indicated meanings and X means chlorine, bromine or iodine, results, under protection of the hydroxy groups (for example by acylation) and optionally diastereomer separation, in the compounds of formula XII.

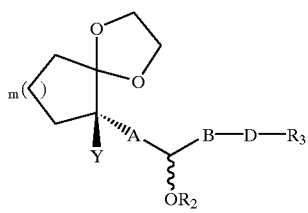

(XII)

The production of the compound of formula XI that is required for the organometallic reaction is carried out by reaction of the corresponding terminal halide with magnesium. By reaction of ketal XII with dilute acetic acid and optionally saponification of the ester and subsequent silylether formation, the ketone of formula XIII is obtained.

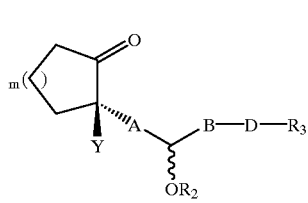

(XIII)

The compounds of formula XII, in which B means a $CH_2$ group and D means a —C≡C group or a CH=CR$_7$ group, can be obtained, for example, by an organometallic reaction of a propargyl halide and subsequent alkylation with a corresponding alkyl halide and optionally subsequent Lindlar hydrogenation.

An alternative structure of the lower chain starts from the aldehyde of formula XIV, which resulted from the Wittig-Horner reaction of aldehyde VI and subsequent reduction and oxidation.

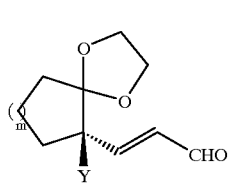

(XIV)

Wittig-Horner olefination of aldehyde XIV with a phosphonate of formula XV

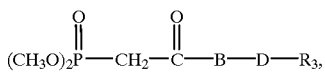

(XV)

and reduction of the ketone that is produced then resulted in an alcohol of formula XII, which optionally can be separated into diastereomers. The protection of the hydroxy group that is now added, for example by acylation, ketal cleavage with acetic acid, optionally saponification of the ester and silylether formation results in the ketone of formula XIII.

The production of the phosphonates of general formula XV that are required for this reaction is described in, for example, DE 42 42 390 or is carried out in a way that is known in the art by reaction of an alkyl halide (that can be produced from the corresponding alcohol by halogenation) of general formula XVI

Hal-D—R$_3$ (XVI)

with the dianion that is produced from the phosphonate of general formula XVII

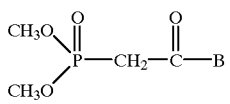

(XVII)

in which B, D and R$_3$ have the above-indicated meanings.

An alternative access to the phosphonates of general formula XV consists in the reaction of the anion of methylphosphonic acid dimethyl ester with an ester of general formula XVIII,

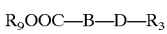

R$_9$OOC—B—D—R$_3$ (XVIII)

in which R$_3$, B, and D have the above-indicated meanings and R$_9$ means an alkyl group with 1–5 C atoms. These esters can be obtained by, for example, alkylation with the corresponding halide.

The incorporation of the chemically and metabolically labile cis-$\Delta^{6,7}$ double bond of LTB$_4$ into a cis-1,2-substituted cycloalkyl ring results in a stabilization, whereby especially by further derivatization of the functional groups and/or structural changes of the lower side chain, LTB$_4$ derivatives that can act as LTB$_4$ antagonists were obtained (DE-A 39 17 597 and DE-A 42 27 790.6 and DE-A 41 08 351 and DE-A 41 39 886.8 and DE-A 42 42 390).

It has now been found that by introducing an alkyl group into the 7-position and by introducing an oxime-ether unit into 5,6-position (numbering system beginning with a carboxyl-C atom with 1 when LTB$_4$ nomenclature is used) in such leukotriene-B$_4$ derivatives, a prolonged duration of action, greater selectivity and better effectiveness can be achieved.

The compounds of formula I act in an antiinflammatory, antiallergic and antiproliferative manner. In addition, the compounds are suitable for lowering elevated triglyceride levels. In addition, they have antimycotic properties. consequently, the new leukotriene-B$_4$ derivatives of formula I represent valuable pharmaceutical active ingredients. The compounds of formula I are suitable for topical and oral administration.

The new leukotriene-B$_4$ derivatives of formula I are suitable in combination with the additives and vehicles that are commonly used in galenical pharmaceutics for topical treatment of diseases of the skin, in which leukotrienes play an important role, e.g.: contact dermatitis, eczemas of the most varied types, neurodermatoses, erythrodermia, pruritus vulvae et ani, rosacea, cutaneus lupus erythematosus, psoriasis, lichen ruber planus et verrucosis and similar skin diseases.

In addition, the new leukotriene-B$_4$ antagonists are suitable for the treatment of multiple sclerosis and symptoms of shock.

The production of the pharmaceutical agent specialties is carried out in the usual way by the active ingredients being converted with suitable additives into the desired form of administration, such as, for example: solutions, ointments, creams or patches.

In the thus formulated pharmaceutical agents, the active ingredient concentration depends on the form of administration. In lotions and ointments, an active ingredient concentration of 0.0001% to 3% is preferably used.

Further, the new compounds optionally in combination with commonly used vehicles and adjuvants are also wellsuited for the production of inhalants, which can be used to treat allergic diseases of the respiratory system, such as, for example, bronchial asthma or rhinitis.

Further, the new leukotriene-$B_4$ derivatives are also suitable in the form of capsules, tablets or coated tablets, which preferably contain 0.1 to 100 mg of active ingredient or are administered orally or in the form of suspensions, which preferably contain 1–200 mg of active ingredient per dosage unit, and are also administered rectally to treat diseases of the internal organs, in which leukotrienes play an important role, such as, e.g.: allergic diseases of the intestinal tract, such as colitis ulcerosa and colitis granulomatosa.

In these new forms of administration, the new $LTB_4$ derivatives, in addition to the treatment of diseases of internal organs with inflammatory processes, are also suitable for the treatment of diseases in which, leukotriene-dependent, the increased growth and the new formation of cells are important. Examples are leukemia (increased growth of white blood cells) or arteriosclerosis (increased growth of smooth muscle cells of blood vessels).

The new leukotriene-$B_4$ derivatives can also be used in combination with, e.g., lipoxygenase inhibitors, cyclooxygenase inhibitors, glucocorticoids, prostacyclin agonists, thromboxane antagonists, leukotriene-$D_4$ antagonists, leukotriene-$E_4$ antagonists, leukotriene-$F_4$ antagonists, phosphodiesterase inhibitors, calcium antagonists, PAF antagonists or other known forms of treatment of the respective diseases.

The following embodiments are used for a more detailed explanation of the process according to the invention.

EXAMPLE 1

(7E)-7{(2S)-2-[(1E,3E,5S)-5-Hydroxy-9-phenyl-6,6-trimethylene-1,3-nonadien-8-inyl]-2-methylcyclohexylidene}-7-aza-6-oxaheptanoic acid-methyl ester 143 mg of (2S)-2-[(5S)-5-tert-butyldimethylsilyloxy-9-phenyl-6,6-trimethylene-1,3-nonadien-8-inyl]-2-methylcyclohexanone is dissolved with 59 mg of hydroxylammonium sulfate in 3.5 ml of methanol, 3.5 ml of tetrahydrofuran and 3.5 ml of water, and it is stirred for 5 hours at room temperature. Then, the reaction mixture is concentrated by evaporation in a vacuum, and the residue is taken up in ether. It is washed with water and saturated sodium bicarbonate solution, dried on sodium sulfate and concentrated by evaporation in a vacuum. The residue is purified by chromatography on silica gel with hexane/ethyl acetate mixtures (gradient: 0–10% ethyl acetate). Yield: 140 mg of the oxime as a colorless oil.

IR (film): 3277, 2930, 2857, 1598, 1490, 1462, 1442, 1360, 1255, 1119, 1063, 992, 942, 836, 775, 755, 691 cm$^{-1}$.

17 mg of sodium hydride (60% dispersion in mineral oil) is added at room temperature to a solution of 140 mg of the above-described oxime in 5 ml of N,N-dimethylformamide, and it is stirred for 1 hour at room temperature. 82 mg of 5-bromovaleric acid-methyl ester is added to it. After two hours of stirring at room temperature, the batch is diluted with ether, washed with 10% citric acid, dried on sodium sulfate and concentrated by evaporation in a vacuum. The residue is purified by chromatography on silica gel with hexane/ethyl acetate mixtures (gradient: 0–10% ethyl acetate). Yield: 160 mg of the ester as a colorless oil.

IR (Film): 2940, 2860, 1740, 1660, 1600, 1440, 1360, 1260, 1210, 1170, 990, 840, 780, 760, 690 cm$^{-1}$.

410 mg of tetrabutylammonium-trihydrate is added to a solution of 160 mg of the above-described ester in 10 ml of tetrahydrofuran. After eight hours of stirring at room temperature, the batch is diluted with ether, washed with water, dried on sodium sulfate and concentrated by evaporation in a vacuum. The residue is purified by chromatography on silica gel with hexane/ether mixtures (gradient: 0–40% ether). Yield: 82 mg of the title compound as a colorless oil. This substance is the preferred embodiment.

IR (Film): 3480, 2920, 2860, 1740, 1600, 1490, 1440, 1370, 1240, 1170, 1090, 990, 920, 755, 690 cm$^{-1}$.

EXAMPLE 2

(7E)-7-{(2S)-2-[(1E,3E,5S)-5-Hydroxy-9-phenyl-6,6-trimethylene-1,3-nonadien-8-inyl]-2-methylcyclohexylidene}-7-aza-6-oxaheptanoic acid 0.75 ml of 1N sodium hydroxide solution is added at room temperature to a solution of 68 mg of the ester, described in Example 1, in 0.8 ml of methanol and 0.8 ml of tetrahydrofuran. After six hours of stirring at room temperature, the batch is acidified with 10% sulfuric acid and extracted with ethyl acetate. The combined organic extracts are washed with saturated sodium chloride solution, dried on sodium sulfate and concentrated by evaporation in a vacuum. The residue is purified by chromatography on silica gel with hexane/ethyl acetate mixtures (gradient: 0–50% ethyl acetate).

Yield: 52 mg of the title compound as a colorless oil.

IR (Film): 3440, 2920, 2860, 1710, 1600, 1490, 1440, 1370, 1240, 1090, 1040, 990, 920, 840, 760, 695 cm$^{-1}$.

EXAMPLE 3

(7E)-7-{(2S)-2-[(1E,3E,5S)-5-Hydroxy-10-phenyl-7,7-trimethylene-1,3-decadien-9-inyl]-2-methylcyclohexylidene}-7-aza-6-oxaheptanoic acid-methyl ester 730 mg of (2S)-2-[(5S)-5-tert-butyldimethylsilyloxy-10-phenyl-7,7-trimethylene-1,3-decadien-9-inyl]-2-methylcyclohexanone is stirred with 290 mg of hydroxylammonium sulfate in 20 ml of methanol, 20 ml of tetrahydrofuran and 20 ml of water for 6 hours at room temperature. The reaction mixture is concentrated by evaporation in a vacuum, and the residue is taken up in ether. It is washed with water and saturated sodium bicarbonate solution, dried on sodium sulfate and concentrated by evaporation in a vacuum. The residue is purified by chromatography on silica gel with hexane/ethyl acetate mixtures (gradient: 0–10% ethyl acetate). Yield: 700 mg of the oxime as a colorless oil.

IR (Film): 3280, 2930, 2860, 1740, 1600, 1490, 1470, 1460, 1440, 1370, 1360, 1250, 1105, 1070, 990, 835, 810, 775, 755, 690 cm$^{-1}$.

24 mg of sodium hydride (60% dispersion in mineral oil) is added to a solution of 200 mg of the above-described oxime in 6 ml of N,N-dimethylformamide. After one hour of stirring at room temperature, it is mixed with 120 mg of 5-bromovaleric acid-methyl ester. After two hours of stirring at room temperature, the batch is diluted with ether, washed with 10% citric acid, dried on sodium sulfate and concentrated by evaporation in a vacuum. The residue is purified by chromatography on silica gel with hexane/ethyl acetate mixtures (gradient: 0–10% ethyl acetate). Yield: 240 mg of the ester as a colorless oil.

IR (Film): 2920, 2860, 1740, 1600, 1490, 1440, 1360, 1255, 1200, 1170, 1070, 990, 840, 775, 755, 690 cm$^{-1}$.

580 mg of tetrabutylammonium fluoride-trihydrate is added to a solution of 230 mg of the above-described ester in 10 ml of tetrahydrofuran. After eight hours of stirring at room temperature, the batch is diluted with ether, washed with water, dried on sodium sulfate and concentrated by evaporation in a vacuum. The residue is purified by chromatography on silica gel with hexane/ether mixtures (gradient: 0–40% ether). Yield: 140 mg of the title compound as a colorless oil.

IR (Film): 3460, 2920, 2860, 1740, 1600, 1490, 1440, 1370, 1250, 1200, 1170, 1100, 1070, 990, 920, 890, 760, 690 cm$^{-1}$.

EXAMPLE 4

(7E)-7-{(2S)-2-[(1E,3E,5S)-5-Hydroxy-10-phenyl-7,7-trimethylene-1,3-decadien-9-inyl]-2-methylcyclohexylidene}-7-aza-6-oxaheptanoic acid 1 ml of 1N sodium hydroxide solution is added at room temperature to a solution of 100 mg of the ester, described in Example 3, in 1.1 ml of methanol and 1.1 ml of tetrahydrofuran. It is stirred for 6 hours at room temperature, acidified with 10% sulfuric acid and extracted with ethyl acetate. The combined extracts are washed with saturated sodium chloride solution, dried on sodium sulfate and concentrated by evaporation in a vacuum. The residue is purified by chromatography on silica gel with hexane/ethyl acetate mixtures (gradient: 0–50% ethyl acetate). Yield: 96 mg of the title compound as a colorless oil.

IR (Film): 3400, 2920, 2860, 1710, 1600, 1490, 1440, 1370, 1240, 1070, 990, 920, 760, 690 cm$^{-1}$.

EXAMPLE 5

(7E)-7-{(2S)-2-[(1E,3E,5S)-5-Hydroxy-10-phenyl-6,6-trimethylene-1,3-decadien-9-inyl]-2-methylcyclohexylidene}-7-aza-6-oxaheptanoic acid-methyl ester 478 mg of (2S)-2-[(5S)-5-tert-butyldimethylsilyloxy-10-phenyl-6,6-trimethylene-1,3-decadien-9-inyl]-2-methylcyclohexanone is stirred with 192 mg of hydroxylammonium sulfate in 13 ml of methanol, 13 ml of tetrahydrofuran and 13 ml of water for 5 hours at room temperature. Then, the reaction mixture is concentrated by evaporation in a vacuum, and the residue is taken up in ether. It is washed with water and saturated sodium bicarbonate solution, dried on sodium sulfate and concentrated by evaporation in a vacuum. The residue is purified by chromatography on silica gel with hexane/ethyl acetate mixtures (gradient: 0–10% ethyl acetate). Yield: 427 mg of the oxime as a colorless oil.

IR (Film): 3273, 2929, 2860, 1598, 1490, 1442, 1360, 1252, 1675, 993, 942, 836, 775, 756, 692 cm$^{-1}$.

46 mg of sodium hydride (60% in mineral oil) is added at room temperature to a solution of 416 mg of the above-described oxime in 13 ml of N,N-dimethylformamide. After one hour of stirring at room temperature, it is mixed with 241 mg of 5-bromovaleric acid-methyl ester. After two hours of stirring at room temperature, the batch is diluted with ether, washed with 10% citric acid, dried on sodium sulfate and concentrated by evaporation in a vacuum. The residue is purified by chromatography on silica gel with hexane/ethyl acetate mixtures (gradient: 0–10% ethyl acetate). Yield: 410 mg of the ester as a colorless oil.

IR (Film): 2929, 2857, 2360, 1741, 1598, 1490, 1442, 1360, 1250, 1168, 1056, 992, 836, 775, 756, 692 cm$^{-1}$.

393 mg of tetrabutylammonium fluoride-trihydrate is added to a solution of 386 mg of the above-described ester in 2.5 ml of tetrahydrofuran. After eight hours of stirring at room temperature, the batch is diluted with ether, washed with water, dried on sodium sulfate and concentrated by evaporation in a vacuum. The residue is purified by chromatography on silica gel with hexane/ether mixtures (gradient: 0–40% ether). Yield: 241 mg of the title compound as a colorless oil.

IR (Film): 3476, 2931, 2840, 1738, 1491, 1442, 1372, 1169, 1070, 993, 757, 692 cm$^{-1}$.

EXAMPLE 6

(7E)-7-{(2S)-2-[(1E,3E,5S)-5-Hydroxy-10-phenyl-6,6-trimethylene-1,3-decadien-9-inyl]-2-methylcyclohexylidene}-7-aza-6-oxaheptanoic acid 9.8 ml of 0.5 N sodium hydroxide solution is added at room temperature to a solution of 235 mg of the ester, described in Example 5, in 10 ml of methanol and 5 ml of tetrahydrofuran. After six hours of stirring at room temperature, the batch is acidified with 10% sulfuric acid and extracted with ethyl acetate. The combined extracts are washed with saturated sodium chloride solution, dried on sodium sulfate and concentrated by evaporation in a vacuum. The residue is purified by chromatography on silica gel with hexane/ethyl acetate mixtures (gradient: 0–50% ethyl acetate).

Yield: 227 mg of the title compound as colorless oil.

IR (Film): 3440, 2930, 2860, 1710, 1600, 1490, 1440, 1370, 1240, 1180, 1090, 1070, 1040, 990, 920, 890, 840, 760, 690 cm$^{-1}$.

EXAMPLE 7

(4E)-4-{(2S)-2-[(1E,3E,5S)-5-Hydroxy-10-phenyl-7,7-trimethylene-1,3-decadien-9-inyl]-2-methylcyclohexyliden}-4-aza-3-oxabutanoic acid 730 mg of (2S)-2-[(5S)-5-tert-butyldimethylsilyloxy-10-phenyl-7,7-trimethylene-1,3-decadien-9-inyl]-2-methylcyclohexanone is stirred with 290 mg of hydroxylammonium sulfate in 20 ml of methanol, 20 ml of tetrahydrofuran and 20 ml of water for 5 hours at room temperature. Then, the reaction mixture is concentrated by evaporation in a vacuum, and the residue is taken up in ether. It is washed with water and saturated sodium bicarbonate solution, dried on sodium sulfate and concentrated by evaporation in a vacuum. The residue is purified by chromatography on silica gel with hexane/ethyl acetate mixtures (gradient: 0–10% ethyl acetate). Yield: 700 mg of the oxime as a colorless oil.

IR (Film): 3280, 2930, 2860, 1740, 1600, 1490, 1470, 1460, 1440, 1370, 1360, 1250, 1105, 1070, 990, 835, 810, 775, 755, 690 cm$^{-1}$.

28 mg of sodium hydride (60% dispersion in mineral oil) is added to a solution of 240 mg of the above-described oxime in 7 ml of N,N-dimethylformamide. After one hour of stirring at room temperature, it is mixed with 120 mg of 2-bromoacetic acid-ethyl ester. After two hours of stirring at room temperature, the batch is diluted with ether, the organic phase is washed with 10% citric acid, dried on sodium sulfate and concentrated by evaporation in a vacuum. The residue is purified by chromatography on silica gel with hexane/ethyl acetate mixtures (gradient: 0–10% ethyl acetate). Yield: 230 mg of the ester as a colorless oil.

IR (Film): 2928, 2856, 2361, 1760, 1738, 1480, 1443, 1373, 1256, 1198, 1103, 933, 890, 836, 775, 756, 692 cm$^{-1}$.

580 mg of tetrabutylammonium fluoride-trihydrate is added to a solution of 220 mg of the above-described ester in 10 ml of tetrahydrofuran. After eight hours of stirring at room temperature, the batch is diluted with ether, washed with water, dried on sodium sulfate and concentrated by evaporation in a vacuum. The residue is purified by chromatography on silica gel with hexane/ether mixtures (gradient: 0–40% ether). Yield: 94 mg of the title compound as a colorless oil.

1 ml of 1N sodium hydroxide solution is added to a solution of 57 mg of the ester in 1 ml of methanol and 1 ml of tetrahydrofuran. After six hours of stirring at room temperature, the batch is acidified with 10% sulfuric acid and extracted with ethyl acetate. The combined organic extracts are washed with saturated sodium chloride solution, dried on sodium sulfate and concentrated by evaporation in a vacuum. The residue is purified by chromatography on silica gel with hexane/ethyl acetate mixtures (gradient: 0–50% ethyl acetate). Yield: 62 mg of the title compound as a colorless oil.

IR (Film): 3440, 2920, 2860, 1700, 1600, 1490, 1440, 1370, 1310, 1090, 1060, 990, 910, 760, 690 cm$^{-1}$.

EXAMPLE 8

(6E)-6-{(2S)-2-[(1E,3E,5S)-5-Hydroxy-10-phenyl-7,7-trimethylene-1,3-decadien-9-inyl]-2-methylcyclohexylidene}-6-aza-5-oxahexanoic acid-methyl ester 730 mg of (2S)-2-[(5S)-5-tert-butyldimethylsilyloxy-10-phenyl-7,7-trimethylene-1,3-decadien-9-inyl]-2-methylcyclohexanone is stirred with 290 mg of hydroxylammonium sulfate in 20 ml of methanol, 20 ml of tetrahydrofuran and 20 ml of water for 6 hours at room temperature. The reaction mixture is concentrated by evaporation in a vacuum, and the residue is taken up in ether. It is washed with water and saturated sodium bicarbonate solution, dried on sodium sulfate and concentrated by evaporation in a vacuum. The residue is purified by chromatography on silica gel with hexane/ethyl acetate mixtures (gradient: 0–10% ethyl acetate). Yield: 700 mg of the oxime as a colorless oil.

IR (Film): 3280, 2930, 2860, 1740, 1600, 1490, 1470, 1460, 1440, 1370, 1360, 1250, 1105, 1070, 990, 835, 810, 775, 755, 690 cm$^{-1}$.

18 mg of sodium hydride (60% dispersion in mineral oil) is added to a solution of 150 mg of the above-described oxime in 5 ml of N,N-dimethylformamide. After one hour of stirring at room temperature, the batch is mixed with 78 mg of 4-bromobutyric acid-trimethylorthoester and stirred for 2 hours at room temperature. It is diluted with ether, the organic phase is washed with 10% citric acid, dried on sodium sulfate and concentrated by evaporation in a vacuum. The residue is purified by chromatography on silica gel with hexane/ethyl acetate mixtures (gradient: 0–10% ethyl acetate). Yield: 180 mg of the ester as a colorless oil.

IR (Film): 2964, 2836, 1739, 1440, 1371, 1301, 1259, 1170, 1093, 961, 916 cm$^{-1}$.

470 mg of tetrabutylammonium fluoride-trihydrate is added to a solution of 180 mg of the above-described ester in 10 ml of tetrahydrofuran. After eight hours of stirring at room temperature, the batch is diluted with ether, washed with water, dried on sodium sulfate and concentrated by evaporation in a vacuum. The residue is purified by chromatography on silica gel with hexane/ether mixtures (gradient: 0–40% ether). Yield: 110 mg of the title compound as a colorless oil.

IR (Film): 3460, 2920, 2860, 1740, 1600, 1490, 1440, 1370, 1320, 1250, 1200, 1170, 1090, 1050, 990, 950, 900, 760, 690 cm$^{-1}$.

EXAMPLE 9

(6E)-6-{(2S)-2-[(1E,3E,5S)-5-Hydroxy-10-phenyl-7,7-trimethylene-1,3-decadien-9-inyl]-2-methylcyclohexylidene}-6-aza-5-oxahexanoic acid 0.8 ml of 1N sodium hydroxide solution is added to a solution of 75 mg of the ester, described in Example 8, in 0.8 ml of methanol and 0.8 ml of tetrahydrofuran. After six hours of stirring at room temperature, the batch is acidified with 10% sulfuric acid and extracted with ethyl acetate. The combined organic extracts are washed with saturated sodium chloride solution, dried on sodium sulfate and concentrated by evaporation in a vacuum. The residue is purified by chromatography on silica gel with hexane/ethyl acetate mixtures (gradient: 0–50% ethyl acetate).

Yield: 62 mg of the title compound as a colorless oil.

IR (Film): 3390, 2920, 1710, 1600, 1490, 1440, 1380, 1370, 1260, 1050, 990, 760, 690 cm$^{-1}$.

EXAMPLE 10

(8E)-8-{(2S)-2-[(1E,3E,5S)-5-Hydroxy-10-phenyl-7,7-trimethylene-1,3-decadien-9-inyl]-2-methylcyclohexyliden}-8-aza-7-oxaoctanoic acid-methyl ester 2.14 g of (2S)-2-[(5S)-5-tert-butyldimethylsilyloxy-10-phenyl-7,7-trimethylene-1,3-decadien-9-inyl]-2-methylcyclohexanone is stirred with 860 mg of hydroxylammonium sulfate in 50 ml of methanol, 50 ml of tetrahydrofuran and 50 ml of water for 5 hours at room temperature. Then, the reaction mixture is concentrated by evaporation in a vacuum and the residue is taken up in ether. It is washed with water and saturated sodium bicarbonate solution, dried on sodium sulfate and concentrated by evaporation in a vacuum. The residue is purified by chromatography on silica gel with hexane/ethyl acetate mixtures (gradient: 0–10% ethyl acetate). Yield: 1.78 g of oxime as a colorless oil.

IR (Film): 3280, 2930, 2860, 1740, 1600, 1490, 1470, 1460, 1440, 1370, 1360, 1250, 1105, 1070, 990, 835, 810, 775, 755, 690 cm$^{-1}$.

24 mg of sodium hydride (60% dispersion in mineral oil) is added to a solution of 200 mg of the above-described oxime in 6 ml of N,N-dimethylformamide. After one hour of stirring at room temperature, the batch is mixed with 133 mg of 6-bromohexanoic acid-ethyl ester. After two hours of stirring at room temperature, the reaction mixture is diluted with ether, washed with 10% citric acid, dried on sodium sulfate and concentrated by evaporation in a vacuum. The residue is purified by chromatography on silica gel with hexane/ethyl acetate mixtures (gradient: 0–10% ethyl acetate). Yield: 260 mg of the ester as a colorless oil.

IR (Film): 2930, 2878, 1736, 1490, 1463, 1373, 1254, 1187, 1070, 992, 836, 776, 756, 692 cm$^{-1}$.

630 mg of tetrabutylammonium fluoride-trihydrate is added to a solution of 260 mg of the above-described ester in 12 ml of tetrahydrofuran. After eight hours of stirring at room temperature, the batch is diluted with ether, washed with water, dried on sodium sulfate and concentrated by evaporation in a vacuum. The residue is purified by chromatography on silica gel with hexane/ether mixtures (gradient: 0–40% ether). Yield: 160 mg of the title compound as a colorless oil.

IR (Film): 3460, 2925, 2860, 1740, 1600, 1490, 1440, 1370, 1160, 990, 910, 760, 690 cm$^{-1}$.

EXAMPLE 11

(8E)-8-{(2S)-2-{(1E,3E,5S)-5-Hydroxy-10-phenyl-7,7-trimethylene-1,3-decadien-9-inyl]-2-methylcyclohexyliden}-8-aza-7-oxaoctanoic acid 1.31 ml of 1N sodium hydroxide solution is added to a solution of 129 mg of the ester, described in Example 10, in 1.4 ml of methanol and 1.4 ml of tetrahydrofuran. After six hours of stirring at room temperature, the batch is acidified with 10% sulfuric acid and extracted with ethyl acetate. The combined organic extracts are washed with saturated sodium chloride solution, dried on sodium sulfate and concentrated by evaporation in a vacuum. The residue is purified by chromatography on silica gel with hexane/ethyl acetate mixtures (gradient: 0–50% ethyl acetate).

Yield: 110 mg of the title compound as a colorless oil.

IR (Film): 3440, 2920, 2860, 1710, 1600, 1490, 1440, 1380, 1240, 1160, 1090, 1050, 990, 920, 755, 690 cm$^{-1}$.

EXAMPLE 12

(7E)-7-{(2S)-2-[(1E,3E,5S)-5-Hydroxy-10-phenyl-7,7-trimethylene-1,3-decadien-9-inyl]-2- methylcyclohexylidene}-7-aza-3,3-dimethyl-6-oxaheptanoic acid-methyl ester 1.3 g of (2S)-2-[(5S)-5-tert-butyldimethylsilyloxy-10-phenyl-7,7-trimethylene-1,3-decadien-9-inyl]-2-methylcyclohexanone is mixed with 522 mg of hydroxylammonium sulfate in 30 ml of methanol, 30 ml of tetrahydrofuran and 30 ml of water. After five hours of stirring at room temperature, the reaction mixture is concentrated by evaporation in a vacuum, and the residue is taken up in ether. It is washed with water and saturated sodium bicarbonate solution, the organic phase is dried on sodium sulfate and concentrated by evaporation in a vacuum. The residue is purified by chromatography on silica gel with hexane/ethyl acetate mixtures (gradient: 0–20% ethyl acetate).

Yield: 1.14 g of the oxime as a colorless oil.

IR (Film): 3270, 2930, 2850, 1740, 1660, 1600, 1490, 1470, 1460, 1440, 1390, 1370, 1360, 1250, 1070, 1050, 990, 940, 835, 810, 775, 755, 690 cm$^{-1}$.

47 mg of sodium hydride (60% dispersion in mineral oil) is added to a solution of 400 mg of the above-described oxime in 5 ml of N,N-dimethylformamide. After one hour of stirring at room temperature, the batch is mixed with 265 mg of 5-bromo-3,3-dimethylpenantoic acid-methyl ester (see Example 12a) and stirred for 2 hours at room temperature. Then, it is diluted with ether, washed with 10% citric acid, dried on sodium sulfate and concentrated by evaporation in a vacuum. The residue is purified by chromatography on silica gel with hexane/ethyl acetate mixtures (gradient: 0–10% ethyl acetate). Yield: 350 mg of the ester as a colorless oil.

IR (Film): 2929, 2857, 1738, 1558, 1540, 1506, 1490, 1472, 1361, 1255, 1073, 992, 937, 836, 775, 756, 692 cm$^{-1}$.

779 mg of tetrabutylammonium fluoride-trihydrate is added to a solution of 320 mg of the above-described ester in 10 ml of tetrahydrofuran. After eight hours of stirring at room temperature, the batch is diluted with ether, washed with water, dried on sodium sulfate and concentrated by evaporation in a vacuum. The residue is purified by chromatography on silica gel with hexane/ether mixtures (gradient: 0–40% ether). Yield: 250 mg of the title compound as a colorless oil.

IR (Film): 3452, 2929, 2825, 1738, 1658, 1598, 1547, 1513, 1490, 1442, 1371, 1224, 1126, 1042, 991, 925, 757, 692 cm$^{-1}$.

EXAMPLE 12a)

5-Bromo-3,3-dimethylpentanoic acid-methyl ester 18 g of sodium borohydride is suspended in 480 ml of 2-propanol. After 30 hours of stirring at room temperature, a solution of 48 g of dimethyl glutaric acid anhydride in 320 ml of 2-propanol is added in drops to it. The reaction mixture is refluxed for 2.5 hours. Then, it is concentrated by evaporation in a vacuum, the residue is poured on ice, acidified with concentrated hydrochloric acid to pH 2 and stirred for 1 hour at room temperature and for 30 minutes at 80° C. It is extracted with ether, the combined extracts are washed with saturated sodium bicarbonate solution and saturated sodium chloride solution, dried on sodium sulfate and concentrated by evaporation in a vacuum. The residue is purified by vacuum distillation (150° C./12 mbar). Yield: 24 g of the lactone as a colorless oil.

IR (Film): 2960, 2870, 1730, 1600, 1485, 1470, 1405, 1370, 1315, 1255, 1175, 1140, 1080, 1040, 1010, 990, 955, 890, 825, 665 cm$^{-1}$.

16 g of hydrogen bromide is introduced into 49 g of acetic acid at 10° C.–23° C. Then, 7 g of the lactone that is produced above in 5 ml of acetic acid is added to it. After 72 hours of stirring at room temperature, the batch is poured onto ice water. The crystals are suctioned off and dissolved in dichloromethane. The solution is dried on sodium sulfate and concentrated by evaporation in a vacuum. The residue is purified by crystallization from hexane.

Yield: 6.9 g of the bromide as white crystals. IR (Film): 2970, 2880, 1710, 1460, 1410, 1390, 1370, 1305, 1250, 1180, 1130, 1090, 1040, 990, 950, 665, 630 cm$^{-1}$.

An ethereal diazomethane solution is slowly added in drops at 0° C. under nitrogen to a solution of 1 g of the bromide, described above, in 10 ml of ether until no more gas generation can be detected. Then, the batch is concentrated by evaporation in a vacuum. The residue is purified by chromatography on silica gel with hexane/ether mixtures (gradient: 0–40% ether). Yield: 1 g of the title compound as a colorless oil.

EXAMPLE 13

(7E)-7-{(2S)-2-[(1E,3E,5S)-5-Hydroxy-10-phenyl-7,7-trimethylene-1,3-decadien-9-inyl]-2-methylcyclohexyliden}-7-aza-3,3-dimethyl-6-oxa-heptanoic acid 2.3 ml of 1N sodium hydroxide solution is added to a solution of 250 mg of the ester, described in Example 12, in 3 ml of methanol and 4 ml of tetrahydrofuran. After six hours of stirring at room temperature, the batch is acidified with 10% sulfuric acid and extracted with ethyl acetate. The combined extracts are washed with saturated sodium chloride solution, dried on sodium sulfate and concentrated by evaporation in a vacuum. The residue is purified by chromatography on silica gel with hexane/ethyl acetate mixtures (gradient: 0–50% ethyl acetate).

Yield: 218 mg of the title compound as a colorless oil.

IR (Film): 3400, 2920, 2860, 1710, 1590, 1570, 1490, 1440, 1370, 1240, 1120, 1090, 1040, 990, 920, 890, 755, 690 cm$^{-1}$.

EXAMPLE 14

(7E)-7-{(2S)-2-[(1E,3E,5S)-5-Hydroxy-10-phenyl-7,7-trimethylene-1,3-decadien-9-inyl]-2-methylcyclohexylidene}-7-aza-3,6-dioxaheptanoic acid-tert-butyl ester 1.3 g of (2S)-2-[(5S)-5-tert-butyldimethylsilyloxy-10-phenyl-7,7-trimethylene-1,3-decadien-9-inyl]-2-methylcyclohexanone is stirred with 522 mg of hydroxylammonium sulfate in 30 ml of methanol, 30 ml of tetrahydrofuran and 30 ml of water for 7 hours at room temperature. Then, the reaction mixture is concentrated by evaporation in a vacuum, and the residue is taken up in ether. It is washed with water and saturated sodium bicarbonate solution, the organic phase is dried on sodium sulfate and concentrated by evaporation in a vacuum. The residue is purified by chromatography on silica gel with hexane/ether mixtures (gradient: 0–20% ether). Yield: 1.14 g of the oxime as a colorless oil.

IR (Film): 3270, 2930, 2850, 1740, 1660, 1600, 1490, 1470, 1460, 1440, 1390, 1370, 1360, 1250, 1070, 1050, 990, 940, 835, 810, 775, 755, 690 cm$^{-1}$.

83 mg of sodium hydride (60% dispersion in mineral oil) is added to a solution of 700 mg of the above-described oxime in 10 ml of N,N-dimethylformamide. After one hour of stirring at room temperature, it is mixed with 347 mg of 2-bromoacetic acid-ethyl ester. After two hours of stirring at room temperature, the batch is diluted with ether, washed with 10% citric acid, dried on sodium sulfate and concentrated by evaporation in a vacuum. The residue is purified by chromatography on silica gel with hexane/ether mixtures (gradient: 0–10% ether). Yield: 740 mg of the ester as a colorless oil.

IR (Film): 2928, 2856, 2359, 1760, 1738, 1598, 1490, 1462, 1444, 1376, 1256, 1198, 1103, 993, 891, 836, 775, 756, 692 cm$^{-1}$.

2.3 ml of diisobutylaluminum hydride (20% in toluene) is added to a solution of 730 mg of the above-described ester in 15 ml of toluene at −60° C. under nitrogen. After 40 minutes, 1 ml of isopropanol and 1 ml of water are added in drops to it. After two hours of vigorous stirring at room temperature, the precipitate is suctioned off and thoroughly washed with ethyl acetate. The combined filtrates are concentrated by evaporation in a vacuum. The residue is purified by chromatography on silica gel with hexane/ether mixtures (gradient: 0–40% ether). Yield: 600 mg of the alcohol as a colorless oil.

IR (Film): 3471, 2926, 2860, 1598, 1490, 1443, 1361, 1256, 1044, 992, 938, 836, 775, 756, 692 cm$^{-1}$.

0.86 ml of 2-bromoacetic acid-tert-butyl ester, 4 ml of 25% sodium hydroxide solution and 36 mg of tetrabutylammonium hydrogen sulfate are added to a solution of 590 mg of the above-described alcohol in 5 ml of toluene. After 16 hours of stirring at room temperature, the batch is diluted with ether, washed with saturated sodium chloride solution, dried on sodium sulfate and concentrated by evaporation in a vacuum. The residue is purified by chromatography on silica gel with hexane/ether mixtures (gradient: 0–20% ether). Yield: 610 mg of the ester as a colorless oil.

IR (Film): 2929, 2857, 1750, 1598, 1490, 1461, 1368, 1254, 1225, 1141, 1071, 992, 936, 836, 776, 756, 692 cm$^{-1}$.

1.4 g of tetrabutylammonium fluoride trihydrate is added to a solution of 580 mg of the above-described ester in 18 ml of tetrahydrofuran. After four hours of stirring at room temperature, the batch is diluted with ether, washed with water, dried with sodium sulfate and concentrated by evaporation in a vacuum. The residue is purified by chromatography on silica gel with hexane/ether mixtures (gradient: 0–40% ether). Yield: 410 mg of the title compound as a colorless oil.

IR (Film): 3477, 2929, 2860, 1748, 1598, 1490, 1443, 1368, 1227, 1141, 1070, 992, 941, 844, 757, 692 cm$^{-1}$.

EXAMPLE 15
(7E)-7-{(2S)-2-[(1E,3E,5S)-5-Hydroxy-10-phenyl-7,7-trimethylene-1,3-decadien-9-inyl]-2-methylcyclohexylidene}-7-aza-3,6-dioxaheptanoic acid 3.6 ml of 1N sodium hydroxide solution is added to a solution of 390 mg of the ester, described in Example 14, in 4 ml of methanol and 4 ml of tetrahydrofuran. After six hours of stirring at room temperature, the batch is acidified with 10% sulfuric acid and extracted with ethyl acetate. The combined extracts are washed with saturated sodium chloride solution, dried on sodium sulfate and concentrated by evaporation in a vacuum. The residue is purified by chromatography on silica gel with hexane/ethyl acetate mixtures (gradient: 0–50% ethyl acetate).

Yield: 331 mg of the title compound as a colorless oil.

IR (Film): 3440, 2920, 2860, 1740, 1600, 1490, 1440, 1370, 1240, 1140, 1070, 990, 940, 910, 755, 690 cm$^{-1}$.

EXAMPLE 16
4-[(3E)-{(2S)-2-[(1E,3E,5S)-5-Hydroxy-10-phenyl-7,7-trimethylene-1,3-decadien-9-inyl]-2-methylcyclohexylidene}-3-aza-2-oxapropyl]benzoic acid-ethyl ester 2.1 g of (2S)-2-[(5S)-5-tert-butyldimethylsilyloxy-10-phenyl-7,7-trimethylene-1,3-decadien-9-inyl]-2-methylcyclohexanone is stirred with 860 mg of hydroxylammonium sulfate in 50 ml of methanol, 50 ml of tetrahydrofuran and 50 ml of water for 5 hours at room temperature. Then, the reaction mixture is concentrated by evaporation in a vacuum, and the residue is taken up in ether. It is washed with water and saturated sodium bicarbonate solution, the organic phase is dried on sodium sulfate and concentrated by evaporation in a vacuum. The residue is purified by chromatography on silica gel with hexane/ethyl acetate mixtures (gradient: 0–10% ethyl acetate). Yield: 1.78 g of the oxime as a colorless oil.

IR (Film): 3280, 2930, 2860, 1740, 1600, 1490, 1470, 1460, 1440, 1370, 1360, 1250, 1105, 1070, 990, 835, 810, 775, 755, 690 cm$^{-1}$.

24 mg of sodium hydride (60% dispersion in mineral oil) is added at room temperature to a solution of 200 mg of the above-described oxime in 6 ml of N,N-dimethylformide. After one hour of stirring at room temperature, the reaction mixture is mixed with 145 mg of 4-(bromomethyl)benzoic acid-ethylester and stirred for 2 hours at room temperature. Then, the batch is diluted with ether, washed with 10% citric acid, dried on sodium sulfate and concentrated by evaporation in a vacuum. The residue is purified by chromatography on silica gel with hexane/ethyl acetate mixtures (gradient: 0–10% ethyl acetate). Yield: 200 mg of the ester as a colorless oil.

IR (Film): 2928, 2856, 1720, 1614, 1490, 1443, 1366, 1275, 1105, 1021, 992, 836, 775, 756, 692 cm$^{-1}$.

470 mg of the tetrabutylammonium fluoride-trihydrate is added to a solution of 200 mg of the above-described ester in 10 ml of tetrahydrofuran. After eight hours of stirring at room temperature, the batch is diluted with ether, washed with water, dried on sodium sulfate and concentrated by evaporation in a vacuum. The residue is purified by chromatography on silica gel with hexane/ether mixtures (gradient: 0–40% ether). Yield: 128 mg of the title compound as a colorless oil.

IR (Film): 3480, 2920, 2860, 1720, 1610, 1600, 1420, 1280, 1180, 1110, 1060, 1020, 990, 890, 850, 760, 690 cm$^{-1}$.

EXAMPLE 17
4-[(3E)-{(2S)-2-[(1E,3E,5S)-5-Hydroxy-10-phenyl-7,7-trimethylene-1,3-decadien-9-inyl]-2-methylcyclohexylidene}-3-aza-2-oxapropyl]benzoic acid 0.97 ml of 1N sodium hydroxide solution is added to a solution of 99 mg of the ester, described in Example 16, in 1 ml of methanol and 1 ml of tetrahydrofuran. After six hours of stirring at room temperature, the batch is acidified with 10% sulfuric acid and extracted with ethyl acetate. The combined organic extracts are washed with saturated sodium chloride solution, dried on sodium sulfate and concentrated by evaporation in a vacuum. The residue is purified by chromatography on silica gel with hexane/ethyl acetate mixtures (gradient: 0–50% ethyl acetate).

Yield: 86 mg of the title compound as a colorless oil.

IR (Film): 3440, 2920, 2860, 1740, 1690, 1610, 1600, 1580, 1440, 1420, 1370, 1310, 1240, 1170, 1100, 1050, 1020, 990, 920, 890, 850, 760, 690 cm$^{-1}$.

EXAMPLE 18
3-[(3E)-{(2S)-2-{(1E,3E,5S)-5-Hydroxy-10-phenyl-7,7-trimethylene-1,3-decadien-9-inyl]-2-methylcyclohexylidene}-3-aza-2-oxapropyl]benzoic acid-methyl ester 730 mg of (2S)-2-[(5S)-5-tert-butyldimethylsilyloxy-10-phenyl-7,7-trimethylene-1,3-decadien-9-inyl]-2-methylcyclohexanone is stirred with 290 mg of hydroxylammonium sulfate in 20 ml of methanol, 20 ml of tetrahydrofuran and 20 ml of water for 5 hours at room temperature. Then, the reaction mixture is concentrated by evaporation in a vacuum, and the residue is taken up in ether.

It is washed with water and saturated sodium bicarbonate solution, dried on sodium sulfate and concentrated by evaporation in a vacuum. The residue is purified by chromatography on silica gel with hexane/ethyl acetate mixtures (gradient: 0–10% ethyl acetate). Yield: 700 mg of the oxime as a colorless oil.

IR (Film): 3280, 2930, 2860, 1740, 1600, 1490, 1470, 1460, 1440, 1370, 1360, 1250, 1105, 1070, 990, 835, 810, 775, 755, 690 cm$^{-1}$.

30 mg of sodium hydride (60% dispersion in mineral oil) is added to a solution of 250 mg of the above-described oxime in 5 ml of N,N-dimethylformamide. After one hour of stirring at room temperature, it is mixed with 170 mg of 3-(bromomethyl)benzoic acid-methyl ester. Then, it is diluted with ether, washed with 10% citric acid, dried on sodium sulfate and concentrated by evaporation in a vacuum. The residue is purified by chromatography on silica gel with hexane/ethyl acetate mixtures (gradient: 0–10% ethyl acetate). Yield: 230 mg of the ester as a colorless oil.

IR (Film): 2920, 2860, 1730, 1600, 1490, 1440, 1430, 1160, 1290, 1250, 1200, 1100, 1070, 990, 900, 840, 810, 775, 755, 720, 690 cm$^{-1}$.

550mg of tetrabutylammonium fluoride-trihydrate is added to a solution of 230 mg of the above-described ester in 10 ml of tetrahydrofuran. After eight hours of stirring at room temperature, the batch is diluted with ether, washed with water, dried on sodium sulfate and concentrated by evaporation in a vacuum. The residue is purified by chromatography on silica gel with hexane/ether mixtures (gradient: 0–40% ether). Yield: 121 mg of the title compound as a colorless oil.

IR (Film): 3480, 2920, 2850, 1720, 1590, 1480, 1440, 1430, 1360, 1280, 1200, 1100, 990, 920, 900, 830, 755, 690 cm$^{-1}$.

EXAMPLE 19

3-[(3E)-{(2S)-2-[(1E,3E,5S)-5-Hydroxy-10-phenyl-7,7-trimethylene-1,3-decadien-9-inyl]-2-methylcyclohexylidene}-3-aza-2-oxapropyl]benzoic acid 0.9 ml of 1N sodium hydroxide solution is added to a solution of 92 mg of the ester, described in Example 18, in 0.9 ml of methanol and 0.9 ml of tetrahydrofuran. After six hours of stirring at room temperature, it is acidified with 10% sulfuric acid and extracted with ethyl acetate. The combined organic extracts are washed with saturated sodium chloride solution, dried on sodium sulfate and concentrated by evaporation in a vacuum. The residue is purified by chromatography on silica gel with hexane/ethyl acetate mixtures (gradient: 0–50% ethyl acetate). Yield: 93 mg of the title compound as a colorless oil.

IR (Film): 3400, 2920, 2860, 1690, 1610, 1590, 1490, 1440, 1370, 1260, 1200, 1100, 1040, 990, 830, 755, 690, 660, 650 cm$^{-1}$.

EXAMPLE 20

4-[(3E)-{(2S)-2-[(1E,3E,5S)-5-Hydroxy-10-phenyl-7,7-trimethylene-1,3-decadien-9-inyl]-2-methylcyclohexylidene}-3-aza-2-oxapropyl}1,3-thiazole 2.1 mg of (2S)-2-[(5S)-5-tert-butyldimethylsilyloxy-10-phenyl-7,7-trimethylene-1,3-decadien-9-inyl]-2-methylcyclohexanone is stirred with 860 mg of hydroxylammonium sulfate in 50 ml of methanol, 50 ml of tetrahydrofuran and 50 ml of water for 5 hours at room temperature. Then, the reaction mixture is concentrated by evaporation in a vacuum, and the residue is taken up in ether. It is washed with water and saturated sodium bicarbonate solution, dried on sodium sulfate and concentrated by evaporation in a vacuum. The residue is purified by chromatography on silica gel with hexane/ethyl acetate mixtures (gradient: 0–10% ethyl acetate). Yield: 1.78 mg of the oxime as a colorless oil.

IR (Film): 3280, 2930, 2860, 1740, 1600, 1490, 1470, 1460, 1440, 1370, 1360, 1250, 1105, 1070, 990, 835, 810, 775, 755, 690 cm$^{-1}$.

48 mg of sodium hydride (60% dispersion in mineral oil) is added to a solution of 200 mg of the above-described oxime in 5 ml of N,N-dimethylformamide. After one hour of stirring at room temperature, it is mixed with 240 mg of 4-(chloromethyl)thiazole-2-carboxylic acid-ethyl ester and stirred for 2 hours at room temperature. Then, it is diluted with ether, the organic phase is washed with 10% citric acid, dried on sodium sulfate and concentrated by evaporation in a vacuum. The residue is purified by chromatography on silica gel with hexane/ethyl acetate mixtures (gradient: 0–10% ethyl acetate). Yield: 247 mg of the ester as a colorless oil.

IR (Film): 2928, 2856, 1712, 1598, 1490, 1462, 1443, 1360, 1253, 1071, 992, 876, 836, 775, 756, 692 cm$^{-1}$.

630 mg of tetrabutylammonium fluoride-trihydrate is added to a solution of 247 mg of the above-described ester in 12 ml of tetrahydrofuran. After eight hours of stirring at room temperature, the batch is diluted with ether, washed with water, dried on sodium sulfate and concentrated by evaporation in a vacuum. The residue is purified by chromatography on silica gel with hexane/ether mixtures (gradient: 0–40% ether). Yield: 82 mg of the title compound as a colorless oil.

IR (Film): 3400, 2920, 2860, 1740, 1720, 1600, 1490, 1440, 1420, 1390, 1300, 1100, 1070, 1060, 990, 920, 880, 840, 760, 690 cm$^{-1}$.

EXAMPLE 20a)

4-(Chloromethyl)thiazole-2-carboxylic acid-ethyl ester 500 mg of oxalic acid-ethyl ester-thioamide and 476 mg of 1,3-dichloroacetone are dissolved in 10 N,N-dimethylformamide and refluxed for 27 hours. Then, it is diluted with ether, washed with water, dried on sodium sulfate and concentrated by evaporation in a vacuum. As a residue, 610 mg of the title compound remains as a colorless oil.

IR (Film): 3105, 2983, 2359, 1716, 1507, 1459, 1391, 1368, 1303, 1255, 1140, 1090, 1017, 970, 862, 758, 715, 656 cm$^{-1}$.

EXAMPLE 21

(6E)-6-{(2S)-2-[(1E,3E,5S)-5-Hydroxy-10-phenyl-7,7-trimethylene-1,3-decadien-9-inyl]-2-methylcyclohexylidene}-6-aza-5-oxa-1,1,1-trifluorohexane 2.1 g of (2S)-2-{(5S)-5-tert-butyldimethylsilyloxy-10-phenyl-7,7-trimethylene-1,3-decadien-9-inyl]-2-methylcyclohexanone is stirred with 860 mg of hydroxylammonium sulfate in 50 ml of methanol, 50 ml of tetrahydrofuran and 50 ml of water for 5 hours at room temperature. Then, the reaction mixture is concentrated by evaporation in a vacuum, and the residue is taken up in ether. It is washed with water and saturated sodium bicarbonate solution, dried on sodium sulfate and concentrated by evaporation in a vacuum. The residue is purified by chromatography on silica gel with hexane/ethyl acetate mixtures (gradient: 0–10% ethyl acetate). Yield: 1.78 mg of the oxime as a colorless oil.

IR (Film): 3280, 2930, 2860, 1740, 1600, 1490, 1470, 1460, 1440, 1370, 1360, 1250, 1105, 1070, 990, 835, 810, 775, 755, 690 cm$^{-1}$.

18 mg of sodium hydride (60% dispersion in mineral oil) is added to a solution of 150 mg of the above-described oxime in 5 ml of N,N-dimethylformamide. After one hour of stirring at room temperature, the reaction mixture is mixed with 110 mg of 4,4,4-trifluoro-1-iodobutane and stirred for 2 hours at room temperature. Then, it is diluted with ether, washed with 10% citric acid, dried on sodium sulfate and concentrated by evaporation in a vacuum. The residue is purified by chromatography on silica gel with hexane/ethyl acetate mixtures (gradient: 0–10% ethyl acetate). Yield: 170 mg of the ester as a colorless oil.

IR (Film): 2929, 2887, 1490, 1443, 1373, 1334, 1253, 1155, 1071, 1025, 991, 836, 775, 756, 691 cm$^{-1}$.

430 mg of tetrabutylammonium fluoride-trihydrate is added to a solution of 170 mg of the above-described ester in 10 ml of tetrahydrofuran. After eight hours of stirring at room temperature, the batch is diluted with ether, washed with water, dried on sodium sulfate and concentrated by evaporation in a vacuum. The residue is purified by chromatography on silica gel with hexane/ether mixtures (gradient: 0–40% ether). Yield: 130 mg of the title compound as a colorless oil.

IR (Film): 3440, 2970, 2860, 1740, 1660, 1600, 1490, 1440, 1370, 1330, 1310, 1250, 1230, 1150, 1070, 1020, 990, 910, 890, 830, 755, 690, 660 cm$^{-1}$.

EXAMPLE 22

(5E)-5-{(2S)-2-[(1E,3E,5S)-5-Hydroxy-9-phenyl-6,6-trimethylene-1,3-nonadien-8-inyl]-2-methylcyclohexylidene}-5-aza-1,1-dimethoxy-4-oxapentane 1.4 g of (2S)-2-[(5S)-5-tert-butyldimethylsilyloxy-9-phenyl-6,6-trimethylene-1,3-nonadien-8-inyl]-2-methylcyclohexanone is stirred with 591 mg of hydroxylammonium sulfate in 35 ml of methanol, 35 ml of tetrahydrofuran and 35 ml of water for 5 hours at room temperature. Then, the reaction mixture is concentrated by evaporation in a vacuum, and the residue is taken up in ether. It is washed with water and saturated sodium bicarbonate solution, the organic phase is dried on sodium sulfate and concentrated by evaporation in a vacuum. The residue is purified by chromatography on silica gel with hexane/ethyl acetate mixtures (gradient: 0–10% ethyl acetate). Yield: 1.36 mg of the oxime as a colorless oil.

IR (Film): 3277, 2930, 2857, 1598, 1490, 1462, 1360, 1255, 1120, 1063, 992, 942, 836, 775, 755, 691 cm$^{-1}$.

36 mg of sodium hydride (60% dispersion in mineral oil) is added to a solution of 300 mg of the above-described oxime in 6 ml of N,N-dimethylformamide. After one-hour of stirring at room temperature, the batch is mixed with 223 mg of 3-bromopropionaldehyde-dimethylacetal and stirred for 2 hours at room temperature. Then, the reaction mixture is diluted with ether, washed with 10% citric acid, dried on sodium sulfate and concentrated by evaporation in a vacuum. The residue is purified by chromatography on silica gel with hexane/ethyl acetate mixtures (gradient: 0–10% ethyl acetate). Yield: 304 mg of the ester as a colorless oil.

IR (Film): 2931, 2857, 1653, 1558, 1506, 1490, 1443, 1388, 1254, 1191, 1125, 1057, 992, 836, 775, 756, 692 cm$^{-1}$.

797 mg of tetrabutylammonium fluoride-trihydrate is added to a solution of 300 mg of the above-described ester in 10 ml of tetrahydrofuran. After eight hours of stirring at room temperature, the batch is diluted with ether, washed with water, dried on sodium sulfate and concentrated by evaporation in a vacuum. The residue is purified by chromatography on silica gel with hexane/ether mixtures (gradient: 0–40% ether). Yield: 209 mg of the title compound as a colorless oil.

IR (Film): 3460, 2930, 2860, 1650, 1620, 1600, 1490, 1440, 1390, 1370, 1190, 1130, 1070, 1060, 990, 920, 760, 690 cm$^{-1}$.

EXAMPLE 23

(7E)-7-{(2S)-2-[(1E,3E,5S)-5-Hydroxy-10-phenyl-7,7-trimethylene-1,3-decadien-9-inyl]-2-methylcyclohexylidene}-7-aza-6-oxaheptanoic acid-5-tetrazolymamide 2.1 g of (2S)-2-[(5S)-5-tert-butyldimethylsilyloxy-10-phenyl-7,7-trimethylene-1,3-decadien-9-inyl]-2-methylcyclohexanone is stirred with 860 mg of hydroxylammonium sulfate in 50 ml of methanol, 50 ml of tetrahydrofuran and 50 ml of water for 13 hours at room temperature. Then, the reaction mixture is concentrated by evaporation in a vacuum, and the residue is taken up in ether. It is washed with water and saturated sodium bicarbonate solution, dried on sodium sulfate and concentrated by evaporation in a vacuum. The residue is purified by chromatography on silica gel with hexane/ethyl acetate mixtures (gradient: 0–10% ethyl acetate). Yield: 1.8 g of the oxime as a colorless oil.

IR (Film): 3270, 2930, 2850, 1740, 1660, 1600, 1490, 1470, 1460, 1440, 1390, 1370, 1360, 1250, 1070, 1050, 990, 940, 835, 810, 775, 755, 690 cm$^{-1}$.

40 mg of sodium hydride (60% dispersion in mineral oil) is added to a solution of 330 mg of the above-described oxime in 7 ml of N,N-dimethylformamide. After one hour of stirring at room temperature, the batch is mixed with 191 mg of 5-bromovaleric acid-methyl ester and stirred for 2 hours at room temperature. Then, the reaction mixture is diluted with ether, washed with 10% citric acid, dried on sodium sulfate and concentrated by evaporation in a vacuum. The residue is purified by chromatography on silica gel with hexane/ethyl acetate mixtures (gradient: 0–10% ethyl acetate). Yield: 380 mg of the ester as a colorless oil.

IR (Film): 2927, 2360, 1738, 1598, 1490, 1435, 1361, 1250, 1168, 1070, 992, 836, 776, 756, 692 cm$^{-1}$.

2.5 ml of 1N sodium hydroxide solution is added to a solution of 380 mg of the above-described ester in 3 ml of methanol and 3 ml of tetrahydrofuran. After 16 hours of stirring at room temperature, the batch is acidified with 1N sulfuric acid to pH 5 and extracted with ether. The combined organic extracts are washed with saturated sodium chloride solution, dried on sodium sulfate and concentrated by evaporation in a vacuum. The residue is purified by chromatography on silica gel with hexane/ethyl acetate mixtures (gradient: 0–50% ethyl acetate). Yield: 280 mg of the acid as a colorless oil.

IR (Film): 2926, 1713, 1598, 1490, 1443, 1372, 1254, 1070, 992, 938, 836, 775, 756, 691 cm$^{-1}$.

50 mg of 5-aminotetrazole and then 100 mg of N,N'-dicyclohexylcarbodiimide in 0.6 ml of tetrahydrofuran are added to a solution of 260 mg of the above-described acid in 1.5 ml of tetrahydrofuran under nitrogen. After 20 hours at room temperature, the precipitate is suctioned off and washed with ethyl acetate. The combined filtrates are concentrated by evaporation in a vacuum. The residue is purified by chromatography on silica gel with hexane/ethyl acetate/methanol mixtures (Gradient: 0–100% ethyl acetate, 0–10% methanol). Yield: 260 mg of the amide as a colorless oil.

IR (Film): 2930, 2860, 1700, 1630, 1600, 1540, 1440, 1400, 1370, 1310, 1250, 1060, 990, 920, 840, 810, 780, 755, 740, 690 cm$^{-1}$.

975 mg of tetrabutylammonium fluoride trihydrate is added to a solution of 260 mg of the above-described amide in 14 ml of tetrahydrofuran. After 8 hours at room temperature, the batch is diluted with ether, washed with water, dried on sodium sulfate and concentrated by evaporation in a vacuum. The residue is purified by chromatography on silica gel with hexane/ether mixtures (gradient: 0–100% ether). Yield: 131 mg of the title compound as a colorless oil.

IR (Film): 3220, 2930, 2860, 1700, 1630, 1590, 1540, 1490, 1450, 1400, 1370, 1310, 1250, 1200, 1130, 1090, 1040, 990, 890, 840, 760, 740, 690 cm$^{-1}$.

EXAMPLE 24

(7E)-7-{(2S)-2-[(1E,3E,5S)-6,6-Dimethyl-5-Hydroxy-9-phenoxy-1,3-nonadienyl]-2-methylcyclohexylidene}-7-aza-3,3-dimethyl-6-oxaheptanoic acid-methyl ester 485 mg of (2S)-2-[(5S)-5-tert-butyldimethylsilyloxy-6,6-dimethyl-9-phenoxy-1,3-nonadienyl]-2-methylcyclohexanone is stirred with 295 mg of hydroxylammonium sulfate in 10 ml of methanol, 10 ml of tetrahydrofuran and 10 ml of water for 5 hours at room temperature. Then, the reaction mixture is concentrated by evaporation in a vacuum, and the residue is taken up in ether. It is washed with water and saturated sodium bicarbonate solution, dried on sodium sulfate and concentrated by evaporation in a vacuum. The residue is purified by chromatography on silica gel with hexane/ethyl acetate mixtures (gradient: 0–10% ethyl acetate). Yield: 347 mg of the oxime as a colorless oil.

IR (Film): 3278, 2930, 2840, 1652, 1601, 1587, 1497, 1471, 1386, 1361, 1301, 1247, 1171, 1109, 1062, 993, 942, 836, 775, 753, 691, 666 cm$^{-1}$.

40 mg of sodium hydride (60% dispersion in mineral oil) is added to a solution of 331 mg of the above-described oxime in 5 ml of N,N-dimethylformamide. After one hour of stirring at room temperature, the batch is mixed with 223 mg of 5-bromo-3,3-dimethylpentanoic acid-methyl ester (Example 12a) and stirred for 2 hours at room temperature. Then, the reaction mixture is diluted with water, washed with 10% citric acid, dried on sodium sulfate and concentrated by evaporation in a vacuum. The residue is purified by chromatography on silica gel with hexane/ethyl acetate mixtures (gradient: 0–10% ethyl acetate). Yield: 348 mg of the ester as a colorless oil.

IR (Film): 2956, 2840, 1738, 1600, 1498, 1471, 1386, 1247, 1110, 1043, 992, 836, 775, 753, 691, 666 cm$^{-1}$.

4.1 g of tetrabutylammonium fluoride-trihydrate is added to a solution of 339 mg of the above-described ester in 10 ml of tetrahydrofuran. After eight hours of stirring at room temperature, the batch is diluted with ether, washed with water, dried on sodium sulfate and concentrated by evaporation in a vacuum. The residue is purified by chromatography on silica gel with hexane/ether mixtures (gradient: 0–40% ether). Yield: 220 mg of the title compound as a colorless oil.

IR (Film): 3500, 2932, 2850, 2358, 1738, 1600, 1586, 1498, 1470, 1387, 1246, 1172, 1040, 991, 928, 754, 692 cm$^{-1}$.

EXAMPLE 25

(7E)-7-{(2S)-[(1E,3E,5S)-6,6Dimethyl-5-Hydroxy-9-phenoxy-1,3-nonadienyl]-2-methylcyclohexylidene}-7-aza-3,3-dimethyl-6-oxaheptanoic acid 1.9 ml of 1N sodium hydroxide solution is added to a solution of 218 mg of the ester, described in Example 24, in 2 ml of methanol and 2 ml of tetrahydrofuran. After six hours of stirring at room temperature, the batch is acidified with 10% sulfuric acid and extracted with ethyl acetate. The combined organic extracts are washed with saturated sodium chloride solution, dried on sodium sulfate and concentrated by evaporation in a vacuum. The residue is purified by chromatography on silica gel with hexane/ethyl acetate mixtures (gradient: 0–50% ethyl acetate).

Yield: 156 mg of the title compound as a colorless oil.

IR (Film): 3440, 2960, 2880, 1710, 1600, 1580, 1500, 1470, 1375, 1260, 1190, 1160, 1040, 990, 930, 920, 760, 690 cm$^{-1}$.

In Vivo Test Systems (i). Production of Human Polymorphonuclear Leukocytes (PMN)

PMNs of healthy volunteers are isolated from heparinized venous blood by dextran sedimentation and subsequent centrifuging via Ficoll-Histopaque®. The remaining erythrocytes are eliminated by hypotonic lysis in 0.2% sodium chloride solution. The PMNs are resuspended in Hank's balanced salt solution (HBSS) and mixed with egg albumin (OVA) or bovine serum albumin (BSA).

(ii). LTB4-Receptor-Competition-Binding Test

Human PMNs are incubated together with OVA with tritium-labeled leukotriene-$B_4$ ($LTB_4$) in the presence or absence of the tested substances at concentrations of 10 $\mu$mol/l to 0.05 mmol/l in HBSS. Cell-bonded, tritium-labeled $LTB_4$ is separated from the free ligands by vacuum filtration by a glass fiber filter and measured in a scintillation measuring device. The non-specific binding of tritium-labeled $LTB_4$ is determined in the presence of excess unlabeled $LTB_4$ (500 nmol/l). Competition factor (CF) is calculated from the ratio of the concentration of the substance to the concentration of the $LTB_4$, which results in a 50% reduction of the tritium-labeled $LTB_4$-receptor bond.

(iii). $LTB_4$-induced Chemotaxis Test

The chemotaxis test is carried out with modified Boyden chambers, which consist of Transwell® modules with polyvinylpyrrolidone-clad polycarbon filters with a pore size of 3 $\mu$m. The upper chamber part contains the human PMNs in HBSS, which is supplemented with BSA or OVA. The lower chamber part is to be added with just buffer or with the chemotactically active leukotriene $B_4$ ($LTB_4$) at a concentration within the limits of 1 nmol/l to 100 nmol/l in the presence or absence of the test substance. The chamber is incubated for 60 minutes in water-saturated atmosphere with 5% carbon dioxide. The number of PMNs, which have found their way into the lower chamber part, is determined in a calibrated test by the measurement of the activity of the enzyme myeloperoxidase (MPO). The enzyme activity is measured by spectrometry (450 nm) by determining the rate of $H_2O_2$-dependent oxidation of aromatic amine 3,3',5,5'-tetramethylbenzidine (TMB).

The $EC_{50}$ value is determined graphically by the non-linear regression curve. The $K_B$ value describes the capabilities of the competitive antagonist. The $K_B$ value is determined as the antagonist concentration that is necessary to raise the $EC_{50}$ value of the agonist by a factor of 2.

The $K_B$ value is calculated as follows:

$$K_B = [LTB_4\text{-receptor-antagonist}]/(DR-1)$$

(DR)=the ratio of the $LTB_4$ concentration that is required for half-maximum stimulation in the presence of the antagonist, to the $LTB_4$ concentration that is required for half-maximum stimulation in the absence of the antagonist.)

(iv). $LTB_4$/iloprost-induced Skin Inflammation in the Ears of Mice

Female NMRI mice with a weight of 26 to 28 g and an age of 5 to 6 weeks are used for this in viva experiment. Ten animals per group are divided at random and kept separate in the various treatment groups. The animals had free access to food and water. To prevent the oral absorption of $LTB_4$/iloprost solutions that are to be administered topically, restraining collars are fastened around the necks of the animals under ether anesthesia shortly before the topical application.

Leukotriene $B_4$ ($LTB_4$) and the stable prostacyclin derivative iloprost is dissolved in ethanol/isopropyl myristat (95+5 v/v) at a concentration of 0.003% (w/v). 10 μl of the $LTB_4$/iloprost solution is administered topically on the outside surface of each ear (surface area about 1 cm²/ear). This corresponds to a dose of 0.3 μg per ear or about 0.3 μg per cm². Animals that are treated with just $LTB_4$/iloprost solution develop the typical features of an inflamed skin with the formation of edemas and infiltration of neutrophiles. These animals are used as positive control animals, that were treated with just ethanol/isopropyl myristat (95+5 v/v) on the outside surface of each ear (surface area of about 1 cm²/ear), are used as a negative control.

The effect of the $LTB_4$-receptor-antagonists on the $LTB_4$/iloprost-induced inflammation reaction is determined either with a topical administration or with an intragastric administration of the test substance.

For the topical application the test substance is dissolved in an LTB4/iloprost solution at various concentrations. 10 μl of this solution is applied topically on the outside surface of the ear.

For intragastric administr ation, the LTB4-receptor-antagonist is dissolved in ethanol. Immediately after the topical administration with LTB4/iloprost, the LTB4-receptor-antagonist or only the solvent is administered intragastrically at various doses with the aid of a probe. The maximum final concentration of ethanol is 3%. The amount of ethanol decreases with additional dilution steps.

The animals are sacrificed 24 hours after the inflammatory reaction sets in. The ears are separated, weighed, flash-frozen and stored for other studies. The peroxidase activity is determined by spectrometry in the homogenate of the ear skin. The tissue is homogenized in HTAB buffer (0.5% hexadecyltrimethylammonium bromide (w/v) in $10^{-3}$ Mol/l of 3-[N-morpholino]propanesulfonic acid with pH 7.0) for 20 seconds with a Polytron® PT 3000 (Kinematica AG, Switzerland) at a rotation of 30,000 rpm. The homogenate is centrifuged for 20 minutes at 10° C. and at 14,500 rpm (20,000 g) in a Sorvall RC2-B centrifuge (SM-24 rotor). The aqueous supernatant is suctioned off and its peroxidase activity is tested at a dilution of 1 to 50 in HTAB buffer. The peroxidase activity is determined by photometric measurement of the rate of $H_2O_2$-dependent oxidation of the aromatic amine 3,3',5,5'-tetramethylbenzidine (TMB). In a 96-hole microtiter plate, the dilute supernatants are incubated with TMB solution and hydrogen peroxide (solution of 6.5 mg of 3,3',5,5'-tetramethylbenzidine dihydrochloride in 1 ml of dimethyl sulfoxide (DMSO); 1:100 (v/v), dissolved with 0.1 mol/l of sodium-acetate-citrate buffer, pH 6.0, final concentration in the incubation mixture: $1.57 \cdot 10^{-4}$ mol/l) (hydrogen peroxide 30% H2O2 1: 16860 (v/v) dissolved with 0.1 mol/l of sodium-acetate-citrate-buffer, pH 6.0, final concentration in the incubation mixture: $4.93 \cdot 10^{-5}$ mol/l). After 30 minutes at room temperature, the reaction is stopped by adding 0.5 mol/l of sulfuric acid. The extinction is determined at 450 nm (maximum absorption) in a microtiter-plate measuring device.

What is claimed is:
1. Leukotriene-$B_4$ derivatives of general formula I

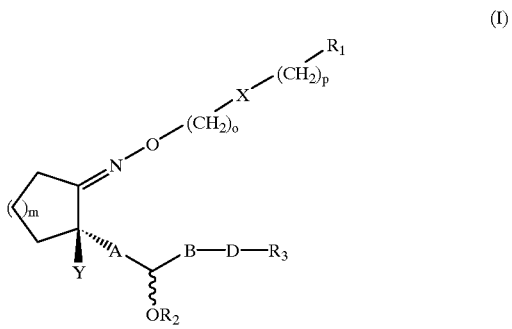

in which
$R_1$ represents H, $CF_3$, $CH_2OH$, $COOR_4$, $CONR_5R_6$, and
$R_2$ represents H or an organic acid radical with 1–15 C atoms,
$R_3$ symbolizes H; $C_1$–$C_{14}$ alkyl, $C_3$–$C_{10}$ cycloalkyl optionally substituted in one or more places; $C_6$–$C_{10}$ aryl radicals, independently of one another, optionally substituted in one or more places by halogen, phenyl, $C_1$–$C_4$ alkyl, $C_1$–$C_4$ alkoxy, fluoromethyl, chloromethyl, trifluoromethyl, carbonyl, carboxyl or hydroxyl; or a 5- to 6-membered aromatic heterocyclic ring with at least 1 heteroatom,
$R_4$ means hydrogen, $C_1$–$C_{10}$ alkyl, $C_3$–$C_{10}$ cycloalkyl; $C_6$–$C_{10}$ aryl radicals optionally substituted by 1–3 halogen, phenyl, $C_1$–$C_4$ alkyl, $C_1$–$C_4$ alkoxy, fluoromethyl, chloromethyl, trifluoromethyl, carboxyl or hydroxyl; $CH_2$—CO—($C_6$–$C_{10}$) aryl or a 5- to 6-membered ring with at least 1 heteroatom,
A symbolizes a trans, trans—CH=CH—CH=CH, a —$CH_2CH_2$—CH=CH— or a tetramethylene group,
B symbolizes a $C_1$–$C_{10}$ straight-chain or branched-chain alkylene group, which optionally can be substituted by fluorine or the group

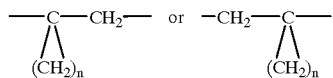

D means a direct bond, oxygen, sulfur, —C≡C—, —CH=$CR_7$, or together with B can also mean a direct bond,
$R_5$ and $R_6$ are the same or different, and represent H or $C_1$–$C_4$ alkyl optionally substituted by hydroxyl groups, or $R_6$ represents H and $R_5$ represents $C_1$–$C_{15}$ alkanoyl or $R_8SO_2$,
$R_7$ means H, $C_1$–$C_5$ alkyl, chlorine, bromine,
$R_8$ has the same meaning as $R_3$,
m means 1–3,
o means 0–5,
p means 0–5,
X is a direct bond, oxygen, sulfur, an aromatic compound or heteroaromatic compound,
Y is a $C_1$–$C_8$ alkyl optionally substituted in one or more places, $C_3$–$C_{10}$ cycloalkyl, optionally substituted by aryl,
n is 2–5,
and, if $R_4$ means hydrogen, their salts with physiologically compatible bases and their cyclodextrin clathrates.

2. Pharmaceutical preparations characterized by a content of leukotriene-B$_4$ derivatives of general formula I according to claim 1.

3. Process for the production of leukotriene-B$_4$ derivatives of general formula I, according to claim 1, characterized in that a ketone of formula II

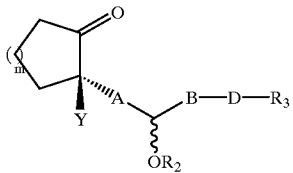
(II)

in which A, B, D, m, R$_2$, R$_3$ and Y have the above-indicated meanings, optionally under protection of free hydroxyl groups in R$_2$, is reacted with a hydroxylamine or a hydroxylammonium salt and then with an alkylating reagent of general formula III, $$E\text{---}(CH_2)_o\text{---}X\text{---}(CH_2)_p\text{---}R_1 \quad (III)$$

whereby E represents a halide or sulfonate, and o, X, p, and R$_1$ have the above-indicated meanings, is reacted in the presence of a base and optionally then separated in any sequence of isomers, protected hydroxyl groups are released and/or a free hydroxyl group is etherified and/or a carboxyl group is reduced and/or a carboxyl group is esterified and/or a carboxyl group is converted into an amide or a carboxyl group is converted into a salt with a physiologically compatible base.

* * * * *